(12) United States Patent
Ochiai et al.

(10) Patent No.: US 9,890,487 B2
(45) Date of Patent: Feb. 13, 2018

(54) LIQUID-RETAINING SHEET AND FACIAL MASK

(71) Applicant: Kuraray Kuraflex Co., Ltd., Okayama-shi (JP)

(72) Inventors: Toru Ochiai, Okayama (JP); Kazuhisa Nakayama, Okayama (JP); Sumito Kiyooka, Kurashiki (JP); Nobuo Araya, Musashino (JP); Naoaki Moritani, Kurashiki (JP)

(73) Assignee: KURARAY KURAFLEX CO., LTD., Okayama-shi (JP)

( * ) Notice: Subject to any disclaimer, the term of this patent is extended or adjusted under 35 U.S.C. 154(b) by 0 days.

(21) Appl. No.: 14/407,720

(22) PCT Filed: Jun. 11, 2013

(86) PCT No.: PCT/JP2013/066069
§ 371 (c)(1),
(2) Date: Dec. 12, 2014

(87) PCT Pub. No.: WO2013/187404
PCT Pub. Date: Dec. 19, 2013

(65) Prior Publication Data
US 2015/0125499 A1    May 7, 2015

(30) Foreign Application Priority Data
Jun. 12, 2012    (JP) .................... 2012-132780

(51) Int. Cl.
| | |
|---|---|
| A45D 44/00 | (2006.01) |
| D04H 1/49 | (2012.01) |
| B32B 5/26 | (2006.01) |
| D04H 1/28 | (2012.01) |
| D04H 1/425 | (2012.01) |
| D06M 11/46 | (2006.01) |
| D06M 15/333 | (2006.01) |
| A61K 8/02 | (2006.01) |
| A61Q 19/00 | (2006.01) |
| B32B 5/02 | (2006.01) |

(Continued)

(52) U.S. Cl.
CPC ............ *D04H 1/49* (2013.01); *A45D 44/002* (2013.01); *A61K 8/0212* (2013.01); *A61Q 19/00* (2013.01); *B32B 5/022* (2013.01); *B32B 5/08* (2013.01); *B32B 5/26* (2013.01); *B32B 7/12* (2013.01); *D04H 1/28* (2013.01); *D04H 1/425* (2013.01); *D04H 1/4258* (2013.01); *D04H 1/465* (2013.01); *D04H 1/492* (2013.01); *D06M 11/46* (2013.01); *D06M 15/333* (2013.01); *B32B 2250/02* (2013.01); *B32B 2260/021* (2013.01); *B32B 2260/046* (2013.01); *B32B 2262/04* (2013.01); *B32B 2262/14* (2013.01); *B32B 2305/22* (2013.01); *B32B 2307/402* (2013.01); *B32B 2307/412* (2013.01); *B32B 2307/54* (2013.01); *B32B 2556/00* (2013.01); *Y10T 442/20* (2015.04); *Y10T 442/626* (2015.04); *Y10T 442/659* (2015.04); *Y10T 442/674* (2015.04); *Y10T 442/689* (2015.04); *Y10T 442/696* (2015.04)

(58) Field of Classification Search
None
See application file for complete search history.

(56) References Cited

U.S. PATENT DOCUMENTS

| | | | |
|---|---|---|---|
| 2007/0219107 A1* | 9/2007 | Nonomura ........... | A61K 8/0208 510/280 |
| 2008/0069845 A1* | 3/2008 | Makihara ............. | A45D 44/002 424/401 |

(Continued)

FOREIGN PATENT DOCUMENTS

| | | |
|---|---|---|
| CN | 1769560 A | 5/2006 |
| CN | 102100640 A | 6/2011 |

(Continued)

OTHER PUBLICATIONS

International Search Report dated Sep. 24, 2013 in PCT/JP2013/066069 Filed Jun. 11, 2013.

(Continued)

*Primary Examiner* — Brian Gulledge
(74) *Attorney, Agent, or Firm* — Oblon, McClelland, Maier & Neustadt, L.L.P.

(57) ABSTRACT

A liquid-retaining sheet contains a liquid-retaining layer that is able to absorb a liquid component, and the liquid-retaining layer is formed from a nonwoven structural member containing a transparent fiber. In the liquid-retaining sheet, the transparency shown below is adjusted to not more than 0.27.

Transparency=Whiteness (%) of a sheet impregnated with 700% by mass of water relative to the sheet mass/Basis weight (g/m²)

The transparent fiber may contain a cellulose-series fiber substantially free from a carboxyl group (in particular, a regenerated cellulose fiber such as a solvent-spinning cellulose-series fiber). The proportion of the solvent-spinning cellulose-series fiber may be not less than 30% by mass in the transparent fiber. The liquid-retaining sheet may be a skin care sheet (in particular, a facial mask) that is impregnated with a liquid component containing a cosmetic preparation. The liquid-retaining sheet has an improved transparency in a wet state in spite of a nonwoven structural member contained in the sheet and shows a suitable strength in a wet state.

20 Claims, 1 Drawing Sheet

(51) Int. Cl.
*D04H 1/4258* (2012.01)
*D04H 1/46* (2012.01)
*B32B 5/08* (2006.01)
*B32B 7/12* (2006.01)
*D04H 1/492* (2012.01)

(56) References Cited

U.S. PATENT DOCUMENTS

2011/0152795 A1* 6/2011 Aledo .................. A61K 8/0212
 604/290
2012/0107387 A1* 5/2012 Ochiai ..................... B32B 5/26
 424/443

FOREIGN PATENT DOCUMENTS

| JP | 2001-170104 A | 6/2001 | | |
|----|---------------|--------|----|----|
| JP | 2004-19033 A | 1/2004 | | |
| JP | 2008-149484 A | 7/2008 | | |
| JP | 2008-255066 A | 10/2008 | | |
| JP | 2008-261067 A | 10/2008 | | |
| JP | 2008-289760 | 12/2008 | | |
| JP | 2009-195373 | 9/2009 | | |
| JP | 2009-299211 A | 12/2009 | | |
| JP | 2010-22484 A | 2/2010 | | |
| JP | 2010-069287 A | 4/2010 | | |
| JP | 2011-126874 A | 6/2011 | | |
| JP | 2011-127267 A | 6/2011 | | |
| JP | 2012-214922 A | 11/2012 | | |
| WO | WO 2011/004834 | * | 1/2011 | ............... D04H 1/54 |
| WO | WO 2011/004834 A1 | 1/2011 | | |

OTHER PUBLICATIONS

Combined Office Action and Search Report dated Sep. 8, 2015 in Chinese Patent Application No. 201380039249.7 (with English language translation).
Office Action dated Oct. 18, 2016, in corresponding Japanese Patent Application No. 2014-521346 (with English-language Translation).
Office Action dated Mar. 7, 2017 in Japanese Patent Application No. 2014-521346 (with English translation).
Combined Chinese Office Action and Search Report dated Nov. 30, 2016 in patent application No. 201380039249.7 with English translation.

* cited by examiner

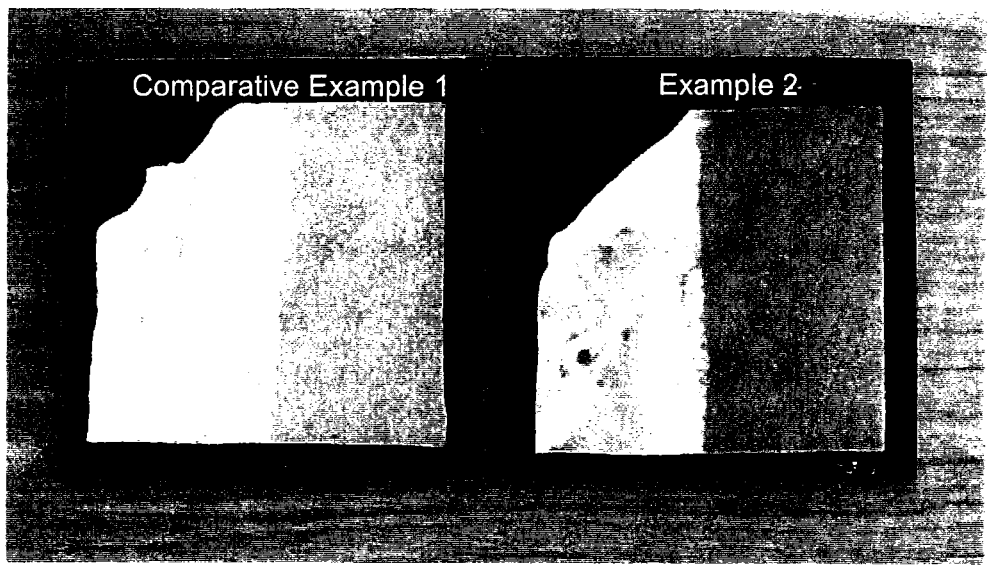

LIQUID-RETAINING SHEET AND FACIAL MASK

TECHNICAL FIELD

The present invention relates to a liquid-retaining sheet which is highly transparent in a wet state in spite of a nonwoven structural member contained in the sheet, and a facial mask formed from the liquid-retaining sheet.

BACKGROUND ART

As a conventional sheet for attachment to the skin of the human body or others, a skin care sheet impregnated with a liquid such as a cosmetic preparation (a liquid-impregnated sheet for living-body application) is being used. The skin care sheet as typified by a facial mask (or a face mask or a facial mask sheet) simply allows the skin to be maintained in a highly wet (or moist) state, and a wide variety of commercial products is now being developed. Among them, the facial mask is formed from a sheet impregnated with a beauty essence and has a function of transferring the beauty essence to the skin. In order to transfer the beauty essence to the skin, the sheet itself requires closely adhering to the skin. Thus, for the purpose of successfully allowing the sheet of the facial mask to have contact with the skin, the sheet itself or the shape of the sheet has a variety of contrivances.

Japanese Patent Application Laid-Open Publication No. 2010-69287 (JP-2010-69287A, Patent Document 1) discloses a three-dimensional mask having a three-dimensional shape fitted to an irregular surface of a user's face; the mask comprises a left-side sheet and a right-side sheet which have mutually symmetrical shapes and each of which has a front edge portion, the front edge portions being opposed with respect to a median line of a user's face, wherein unattached portions of the left-side sheet and the right-side sheet are alienated from each other by bonding the front edge portions to each other with the surfaces of the front edge portions curved outward.

Unfortunately, the three-dimensional mask has an insufficient adhesion. In practical use, a user adjusts a portion that is out of close adhesion to the user's skin (a portion having a gap between the sheet and the user's skin) under pressure of the user's finger so as to allow the mask to closely adhere to the user's skin.

Meanwhile, as a material for a facial mask, a woven or nonwoven fabric made of fibers is commonly used. Patent Document 1 also discloses that the material for the three-dimensional mask includes a nonwoven fabric or a woven fabric, although Patent Document 1 is silent on the details of the nonwoven fabric or the woven fabric. Incidentally, a material to be commonly used for a facial mask includes a spunlace nonwoven fabric containing a cellulose-series fiber as a main component, as typified by a highly hydrophilic cotton.

International Publication WO2011/004834 (Patent Document 2) discloses a facial mask comprising a liquid-retaining layer and an adhesion layer; the liquid-retaining layer comprises a first nonwoven structural member comprising a first fiber and has an ability to absorb a liquid component, and the adhesion layer is contactable with a skin, is formed on at least one side of the liquid-retaining layer and is permeable to the liquid component, wherein the adhesion layer comprises a second nonwoven structural member comprising a second fiber, and the second fiber has a number-average fiber diameter of not more than 10 μm, and the thickness ratio of the adhesion layer relative to the liquid-retaining layer is 1/4 to 1/100 as a ratio of the adhesion layer/the liquid-retaining layer.

Unfortunately, this facial mask also has an insufficient adhesion to a skin. Meanwhile, a facial mask not only plays a role in skin care but also serves as a luxury (or discretionary) item for women. Thus the facial mask is required to have a high beauty effect and a high-grade feeling. In order to satisfy the beauty effect and the high-grade feeling, the quantity of an expensive beauty essence is increased. Thus, to retain the liquid (or the beauty essence), the facial mask is designed to have a high basis weight. Consequently, the facial mask is opaque, and it is difficult to visually confirm whether the facial mask is closely adhering to the skin during use.

Japanese Patent Application Laid-Open Publication No. 2001-170104 (JP-2001-170104A, Patent Document 3) discloses a cosmetic pack which comprises a nonwoven fabric composed of a carboxymethyl cellulose fiber and is allowed to swell in water or an aqueous solution at a time of use to cover a predetermined place of the skin.

Japanese Patent Application Laid-Open Publication No. 2011-127267 (JP-2011-127267A, Patent Document 4) discloses a porous cellulose gel that comprises a nonwoven fabric composed of a cellulose fiber having a carboxyl group chemically introduced thereinto by oxidizing only a primary hydroxyl group at the C-6 site in a glucose residue, and a liquid absorbed in the nonwoven fabric; the oxidized cellulose fiber has a substitution degree of 0.1 to 0.6. This document also discloses that the porous gel can be used for a cosmetic pack material.

Unfortunately, the nonwoven fabrics described in Patent Documents 3 and 4 have a low strength in a wet state, because the nonwoven fabrics, which are transparent, are obtained by gelating an extremely highly water-absorbing cellulose fiber having a carboxyl group. Thus each one of facial masks made of the nonwoven fabrics lacks a strength required to stretching of about 20 to 40% in a wet state and is hard to attach. It is difficult to allow the facial mask to fully adhere to (or fit with) the skin.

RELATED ART DOCUMENTS

Patent Documents

Patent Document 1: JP-2010-69287A (Claims, paragraphs [0019] [0039])
Patent Document 2: International Publication WO2011/004834 (Claims)
Patent Document 3: JP-2001-170104A (Claims, Examples)
Patent Document 4: JP-2011-127267A (Claim 1, paragraphs [0001] [0012], Examples)

SUMMARY OF THE INVENTION

Problems to be Solved by the Invention

It is therefore an object of the present invention to provide a liquid-retaining sheet having an improved transparency in a wet state (or a wet condition) although the sheet contains a nonwoven structural member and showing a suitable (or appropriate) strength in a wet state (or a wet condition), and a facial mask formed from the liquid-retaining sheet.

Another object of the present invention is to provide a liquid-retaining sheet that can accelerate absorption of an effective ingredient contained in an impregnated liquid component, and a facial mask formed from the liquid-retaining sheet.

It is still another object of the present invention to provide a liquid-retaining sheet having a balance kept between a liquid retentivity and a liquid releasability, as well as having improved adhesion and fit (or conformity) to the skin in the state where the sheet is impregnated with a liquid component; and a facial mask formed from the liquid-retaining sheet.

Means to Solve the Problems

The inventors of the present invention made intensive studies to achieve the above objects and finally found that, for a liquid-retaining sheet containing a liquid-retaining layer that is able to absorb a liquid component and is formed from a nonwoven structural member containing a transparent fiber, the liquid-retaining sheet has an improved transparency in a wet state and shows a suitable (or appropriate) strength in a wet state in spite of the nonwoven structural member contained in the sheet by forming the nonwoven structural member from a specified fiber to adjust the whiteness of the nonwoven structural member. The present invention was accomplished based on the above findings.

That is, the present invention includes a liquid-retaining sheet (or a liquid-retention sheet) containing a liquid-retaining layer (or a liquid-retention layer) that is able to absorb a liquid component; the liquid-retaining layer has (or is formed from) a nonwoven structural member containing a transparent fiber. The liquid-retaining sheet has a transparency shown below of not more than 0.27.

Transparency [%/(g/m$^2$)]=Whiteness (%) of a sheet impregnated with 700% by mass of water relative to the sheet mass/Basis weight (g/m$^2$)

The transparent fiber may contain a cellulose-series fiber (in particular, a regenerated cellulose fiber such as a solvent-spinning cellulose fiber) substantially free from a carboxyl group. The transparent fiber may contain a rayon fiber in addition to the solvent-spinning cellulose fiber. The proportion of the solvent-spinning cellulose fiber may be not less than 30% by mass in the (whole) liquid-retaining layer. The transparent fiber may have a coloring agent (such as titanium oxide) content of not more than 0.1% by mass. The nonwoven structural member may contain (or may be formed from) a staple (transparent) fiber having an average fiber diameter of 1 to 15 µm. The staple fiber may have an average fiber length of about 20 to 70 mm. The nonwoven structural member may have an apparent density of 0.08 to 0.15 g/cm$^3$ and a void ratio of 90 to 95%. The nonwoven structural member may contain a spunlace nonwoven fabric obtainable by hydroentangling a semi-random web, a parallel web, or a cross web. The nonwoven fabric member may have a basis weight of about 30 to 100 g/m$^2$.

The liquid-retaining sheet of the present invention may further contain a nonporous transparent layer over a first side of the liquid-retaining layer. The nonporous transparent layer may contain a transparent resin.

The liquid-retaining sheet of the present invention may further contain an adhesion layer over at least one side of the liquid-retaining layer. The adhesion layer may contain (or be formed from) a meltblown nonwoven fabric. The meltblown nonwoven fabric may contain a transparent fiber having a coloring agent content of not more than 0.1% by mass.

The liquid-retaining sheet of the present invention may have a stress at 30% elongation of not less than 1.5 N/5 cm in at least one direction under wetting in accordance with JIS (Japanese Industrial Standards) L 1913.

In a case where the liquid-retaining sheet of the present invention is impregnated with 700% by mass of water relative to the sheet mass (the mass of the sheet), the liquid-retaining sheet may have a whiteness (%) of about 1 to 10%.

The liquid-retaining sheet of the present invention may be a sheet in which the liquid-retaining layer is impregnated with a liquid component, for example, may be a skin care sheet (in particular, a facial mask (a face mask, a facial sheet mask)) in which the liquid-retaining layer is impregnated with a liquid component containing a cosmetic preparation.

As used herein, the term "skin care" means not only the use of a cosmetic preparation, a milky lotion, and the like to look after the skin (typical skin care) but also wider concepts including other actions which can be associated with the skin (contact with the skin). Thus the skin care sheet (or sheet for skin care) may include, for example, a sheet to be applied (or touched) to the skin, e.g., a sheet for washing the skin, a sheet for relieving an skin itching, a sheet for cooling through the skin, and a sheet for reducing an inflammation and other symptoms by penetration (or infiltration) in the skin (e.g., a compress).

Effects of the Invention

According to the present invention, since the liquid-retaining sheet, which contains a liquid-retaining layer formed from a nonwoven structural member, is highly transparent, the sheet can improve in transparency in a wet state in spite of the nonwoven structural member contained in the sheet and show a suitable strength in a wet state. Thus use of the sheet as a facial mask facilitates visual confirmation whether the sheet is in close adhesion to the skin during use. In addition, since the sheet has a strength suitable for stretching of about 20 to 40% in a wet state, the sheet is easy to attach. Thus it is easy to allow the sheet to fully adhere to (or fit with) the skin. Moreover, lamination of a nonporous transparent layer formed from a transparent resin on or over a first side of the liquid-retaining layer can accelerate absorption to the skin of an effective ingredient contained in a liquid component with which the liquid-retaining layer is impregnated. Further, lamination of an adhesion layer formed from a meltblown nonwoven fabric on or over at least one side of the liquid-retaining layer can maintain the balance between liquid retentivity and liquid releasability and improve the adhesion and fit (or conformity) to the skin in the state where the sheet is impregnated with a liquid component.

BRIEF DESCRIPTION OF DRAWINGS

FIG. 1 is a photographic comparison of wet states of liquid-retaining sheets obtained in Example 2 and Comparative Example 1.

DESCRIPTION OF EMBODIMENTS

[Liquid-Retaining Layer]

The liquid-retaining sheet (or liquid-retention sheet) of the present invention contains a liquid-retaining layer (or liquid-retention layer) having an ability to absorb a liquid component (in particular, an aqueous liquid component). Specifically, according to the present invention, the liquid-retaining layer has a wettability necessary to impregnate a liquid component (liquid compound or composition) containing a beauty ingredient or a medicinal (effective) ingredient [for example, a moisturizing ingredient, a cleansing ingredient, an antiperspirant ingredient, an aroma (or fragrance) ingredient, a whitening (or skin-lightening) ingredient, a blood-circulation-promoting ingredient, a cooling ingredient, an ultraviolet-ray-absorbing ingredient, and an anti-itch ingredient for skin] and voids for retaining (or holding) the liquid component. When handled, the liquid-retaining layer retains (or holds) the liquid component without dripping from the layer until a predetermined site of the body (e.g., the face) is covered with the sheet. The liquid-retaining sheet is attached to or laid on the skin, and then the liquid-retaining layer plays a role in gradually allowing to move (or transfer) the liquid composition toward the skin. According to the present invention, the liquid-retaining layer having such characteristics is formed from a nonwoven structural member.

The nonwoven structural member constituting the liquid-retaining layer contains a high-purity transparent fiber in the light of improvement of transparency in a wet (or moist) state. The transparent fiber may have a purity of not less than 99.5% by mass, for example, about 99.5 to 100% by mass, preferably about 99.7 to 99.99% by mass, and more preferably about 99.8 to 99.98% by mass (particularly, about 99.9 to 99.95% by mass). A transparent fiber having a low purity reduces the transparency of the liquid-retaining sheet in a wet state.

Further, in the light of improvement of transparency, the transparent fiber has a high purity and, in addition, is preferably free from a coloring agent (in particular, an opaque coloring agent). The coloring agent content of the transparent fiber may for example be not more than 0.1% by mass (e.g., about 0 to 0.1% by mass), preferably not more than 0.09% by mass, and more preferably not more than 0.08% by mass or may be not more than 0.01% by mass (e.g., about 0 to 0.01% by mass). In a case where the coloring agent content is too large, the liquid-retaining sheet has a low transparency in a wet state. Incidentally, since a commercially available fiber usually contains an inorganic pigment (in particular, titanium oxide) in terms of fiber-forming property, the coloring agent content may be an inorganic pigment (in particular, titanium oxide) content.

The transparent fiber may contain a coloring agent (particle) without losing the transparency of the fiber due to the condensation (or aggregation) of the coloring agent. For example, the transparent fiber may contain a coloring agent having a particle diameter shorter than a wavelength of a visible ray. Thus the opaque coloring agent that is not contained in the transparent resin may have a particle diameter of, for example, not less than 0.01 µm (e.g., about 0.01 to 1 µm), preferably not less than 0.1 µm (e.g., about 0.1 to 0.8 µm), and more preferably not less than 0.2 µm (e.g., about 0.2 to 0.6 µm).

The transparent fiber may include, for example, a fiber containing (or formed from) a resin component, such as a polyolefin-series resin, an acrylic resin, a poly(vinyl acetal)-series resin, a poly(vinyl chloride)-series resin, a poly(vinylidene chloride)-series resin, a polyester-series resin, a polyamide-series resin, a polyurethane-series resin, or a cellulose-series resin. These transparent fibers may be used alone or in combination.

Among these transparent fibers, in order to ensure the wettability or the liquid retentivity, a transparent fiber containing a fiber composed of a hydrophilic resin is preferred. In a case where a liquid (such as a cosmetic preparation) is added to the liquid-retaining sheet, the fiber containing the hydrophilic resin plays an important role in incorporating the liquid into the inside of the nonwoven structural member and also plays a role of retaining a large quantity of the cosmetic preparation liquid once incorporated into the nonwoven structural member without dripping in handling in use.

The hydrophilic fiber is not particularly limited to a specific one as far as the fiber has a hydrophilicity. As the hydrophilic fiber, a synthetic fiber, a natural fiber, a regenerated fiber, and other fibers may be selected. The regenerated fiber is produced by dissolving a natural plant fiber or an animal protein fiber and then regenerating the dissolved matter with a chemical treatment. Further, it is sufficient that the hydrophilic fiber comprises a hydrophilic resin in at least a surface thereof. For example, the hydrophilic fiber may include a resin in which a hydrophobic resin is treated to impart hydrophilicity to a surface thereof, a conjugated fiber (or a conjugate fiber) containing a core composed of a hydrophobic resin, and others.

The synthetic fiber may include, for example, a synthetic fiber which comprises a resin having a hydrophilic group such as a hydroxyl group, a carboxyl group, or a sulfonic acid group (particularly a hydroxyl group) in a molecule thereof [for example, a poly(vinyl alcohol)-series resin, a polyamide-series resin, or a polyester-series resin such as a poly(lactic acid); a (meth)acrylic copolymer containing a (meth)acrylamide unit; and others]. These synthetic fibers may be used alone or in combination. Among these synthetic fibers, a hydrophilic resin having a hydroxyl group in a monomer unit thereof is preferred. In particular, from the viewpoint of a uniform distribution of hydroxyl groups in a molecule, a fiber containing an ethylene-vinyl alcohol-series copolymer is preferred.

For the ethylene-vinyl alcohol-series copolymer, the ethylene unit content (the ratio of the ethylene unit in the copolymer) is, for example, about 10 to 60 mol %, preferably about 20 to 55 mol %, and more preferably about 30 to 50 mol %. The saponification degree of the vinyl alcohol unit is, for example, about 90 to 99.99 mol %, preferably about 95 to 99.98 mol %, and more preferably about 96 to 99.97 mol %. The viscosity-average degree of polymerization is, for example, about 200 to 2500, preferably about 300 to 2000, and more preferably about 400 to 1500. As described later, a thermal adhesive resin under moisture (or moistenable-thermal adhesive resin, moistenable adhesive resin under heat, or adhesive resin under heat and moisture), such as an ethylene-vinyl alcohol-series copolymer, can be used to form a bulky and stable liquid-retaining layer by a steam jet method.

Examples of the natural fiber may include a cotton, a silk, a flax (or a linen), a silk, and a wool. These natural fibers may be used alone or in combination. Among them, a cotton or the like is widely used.

The regenerated fiber may include, for example, a cellulose-series fiber, such as a rayon (e.g., a viscose rayon), an acetate, a lyocell [such as TENCEL (registered trademark)], a cupra (cupro), or a polynosic. These fibers may be used alone or in combination. Among them, a rayon fiber or a Tencel fiber is widely used.

Regarding the fiber of which a surface comprises a hydrophilic resin, a method for imparting a hydrophilicity to a surface of a fiber may include a method which comprises making a fiber-formable (or fiber-forming) resin and a hydrophilic resin into a fibrous form to cover at least a region of the fiber surface with the hydrophilic resin. A conjugated fiber formed by the method of covering the fiber surface with the hydrophilic resin is preferred because of less deterioration in hydrophilicity even when used for a long time. Moreover, the method of making a fiber-formable resin and a hydrophilic resin into a fibrous form is preferred in view of the shortening of the production process and the achievement of a uniformly high hydrophilicity. In particular, in the respect of a high hydrophilicity, it is preferred to use a fiber having a whole surface thereof covered with a hydrophilic resin in a sheath form, that is, a conjugated fiber having a sheath-core structure in which the sheath comprises a hydrophilic resin.

The sheath-core structure conjugated fiber is not particularly limited to a specific one as far as the sheath comprises a hydrophilic resin. The core preferably comprises a hydrophobic resin for the after-mentioned hydrophobic fiber in order to maintain the form (or shape) of the fiber even in the impregnation with the liquid component and prevent the deterioration of the permeability. Further, among the hydrophobic resins, for example, the preferred resin includes a polypropylene-series resin, a polyester-series resin, and a polyamide-series resin. In particular, in view of a well-balanced heat resistance, fiber-forming property, and the like, a polyester-series resin [e.g., a poly(ethylene terephthalate)] is preferred. Incidentally, in view of the production of a bulky and stable nonwoven fabric, or the others, the preferred hydrophilic resin for the sheath includes a resin for a synthetic fiber, particularly, a poly(vinyl alcohol)-series resin such as an ethylene-vinyl alcohol-series copolymer. For the sheath-core structure conjugated fiber, the ratio (mass ratio) of the core relative to the sheath [the sheath/the core] is, for example, about 90/10 to 10/90 (e.g., about 80/20 to 10/90), preferably about 80/20 to 15/85, and more preferably about 60/40 to 20/80.

Moreover, among these hydrophilic fibers, a cellulose-series fiber (e.g., a rayon and Tencel) is permeable to water or an aqueous solution, a polar solvent, or an emulsion thereof which constitute the liquid component (e.g., a cosmetic preparation) to the inside of the fiber and has an excellent absorbability and a high liquid retentivity. In these respects, the cellulose-series fiber is particularly preferred. On the other hand, an ethylene-vinyl alcohol-series copolymer fiber (particularly, a sheath-core structure conjugated fiber in which the sheath comprises an ethylene-vinyl alcohol-series copolymer) is inferior to the cellulose-series fiber in liquid retentivity. However, the ethylene-vinyl alcohol copolymer fiber has an excellent adaptability to the liquid component (e.g., a cosmetic preparation), the fiber itself does not absorb the liquid component, and the liquid component is easily released under a pressure or other means. In these respects, the ethylene-vinyl alcohol copolymer fiber is particularly preferred. Accordingly, the cellulose-series fiber and the ethylene-vinyl alcohol-series copolymer fiber may be selected depending on the viscosity or quantity of the liquid component (e.g., a cosmetic preparation). Further, the liquid retentivity and liquid releasability may be controlled by mixing these fibers. Furthermore, if necessary, other fibers may be added to the fiber(s).

According to the present invention, the cellulose-series fiber is preferred in view of an excellent balance between the transparency and the liquid retentivity in a wet state. A particularly preferred fiber includes a solvent-spinning cellulose fiber (e.g., a lyocell such as Tencel) obtained by a solvent spinning method (a direct method in which a cellulose is not chemically converted once).

The cellulose-series fiber preferably has a suitable (appropriate) hydrophilicity in order to retain a suitable strength under wetting. The cellulose-series fiber preferably includes a cellulose-series fiber substantially free from a carboxyl group (or carboxymethyl group). Specifically, the carboxyl group (or carboxymethyl group) in the cellulose skeleton of the cellulose-series fiber may have an average substitution degree of less than 0.05, for example, not more than 0.03, preferably not more than 0.01 (e.g., about 0 to 0.01), and more preferably not more than 0.001 (in particular, substantially zero). In a case where the carboxyl group content is too large, the nonwoven fabric has a low strength under wetting due to gelation under wetting.

The hydrophilic fiber has an excellent liquid retentivity. The hydrophilic fiber may have a water retention at a basis weight of 50 g/m$^2$ of not less than 500%, for example, about 500 to 3000%, preferably about 800 to 2500%, and more preferably about 1000 to 2000% (particularly, about 1100 to 1500%).

In the description of this application, the water retention was measured by providing a sheet-like nonwoven fabric (or a nonwoven fabric sheet) having a basis weight of 50 g/m$^2$ and a size of 5 cm×5 cm, pinching one end of the fabric with a clip, immersing the fabric in water for 30 seconds, dripping water from the fabric with the fabric left for one minute in a condition that the plane surface of the fabric was parallel to the gravitational direction, then weighing the fabric, and determining the water retention based on the following equation:

$$\text{Water retention}=[(B-A)/A]\times 100$$

wherein A is the weight of the nonwoven fabric before immersion, B is the weight of the nonwoven fabric after water drip.

In order to achieve an excellent balance between the liquid retentivity and the liquid releasability and improve the structural stability of the liquid-retaining layer, the hydrophilic fiber may be used in combination with a hydrophobic fiber or a nonhydrophilic fiber (a fiber having a polarity which is not so high and a relatively strong hydrophobicity). The Young's modulus of the hydrophobic fiber hardly decreases even when the liquid-retaining layer is in a wet (or moist) state. Thus the hydrophobic fiber performs to maintain the bulkiness or stiffness of the liquid-retaining layer.

The hydrophobic fiber is not particularly limited to a specific one and may include a fiber which comprises a resin having an official regain of less than 2.0% in a standard state (20° C., 65% RH). Examples of the resin may include a resin commonly used for nonwoven fabric, e.g., a polyolefin-series resin (e.g., a polyethylene and a polypropylene), a polyester-series resin [e.g., a poly(ethylene terephthalate), a poly(butylene terephthalate), and a poly(ethylene naphthalate)], a polyamide-series resin (e.g., a polyamide 6, a polyamide 6,6, and a polyamide 4,6), a polyurethane-series resin (e.g., a polyesterpolyol-based urethane-series resin), and a polyacrylonitrile-series resin. These hydrophobic fibers may be used alone or in combination. Among them, in terms of high versatility, excellent mechanical properties, or others, a polyester fiber is preferred.

The ratio of the hydrophilic fiber relative to the hydrophobic fiber (mass ratio) [the former/the latter] may be selected from about 100/0 to 1/99. In the light of the liquid retentivity, the proportion of the hydrophilic fiber (in particular, a cellulose-series fiber) in the liquid-retaining layer is preferably at least 30% by mass or more. In a case where the liquid-retaining layer contains both fibers, the ratio (mass ratio) of the hydrophilic fiber relative to the hydrophobic fiber [the former/the latter] is about 99/1 to 30/70, preferably about 90/10 to 35/65, and more preferably about 80/20 to 30/70 (particularly, about 70/30 to 40/60). When the ratio of the hydrophilic fiber is excessively small, the resulting unadaptability of the liquid-retaining sheet to the liquid component causes an uneven liquid quantity in the liquid-retaining sheet, a low capability of the liquid-retaining sheet to retain the liquid component, or a dripping from the liquid-retaining sheet in use. On the other hand, when the ratio of the hydrophilic fiber is excessively large, the capability of the liquid-retaining sheet to retain the liquid component becomes high. Thus, since it is difficult to release the liquid cosmetic preparation toward the skin in use or an excessive quantity of the liquid component is needed beforehand to secure a necessary releasing quantity, the liquid component is often used wastefully.

The transparent fiber may further contain a conventional additive as far as the transparency is not impaired. The conventional additive may include, for example, a stabilizer (e.g., a heat stabilizer such as a copper compound, an ultraviolet absorber, a light stabilizer, and an antioxidant), a dispersing agent, a particulate (or fine particle), an antistatic agent, a flame-retardant, a plasticizer, a lubricant, and a crystallization speed retardant. These additives may be used alone or in combination. The additive may adhere on (or may be supported to) a surface of the liquid-retaining layer or may be contained in the fiber.

The liquid-retaining layer may contain an opaque fiber [e.g., a fiber containing an inorganic pigment (such as titanium oxide)] in addition to the transparent fiber as far as the transparency is not impaired. The proportion of the transparent fiber (in particular, a solvent-spinning cellulose fiber) in the (whole) liquid-retaining layer may be not less than 70% by mass, for example, about 70 to 100% by mass, preferably about 80 to 100% by mass, and more preferably about 90 to 100% by mass (particularly, about 95 to 100% by mass). The transparent fiber may be contained alone in the liquid-retaining layer. In a case where the proportion of the transparent fiber is too small, the liquid-retaining layer has a low transparency in a wet state.

In particular, in order to maintain a high transparency in a wet state and a suitable strength in a wet state and possess an improved easiness of handling as a facial mask, it is preferred to increase the proportion of the solvent-spinning cellulose fiber in the liquid-retaining layer. The proportion of the solvent-spinning cellulose fiber in the (whole) liquid-retaining layer may be not less than 30% by mass, for example, about 50 to 100% by mass, preferably about 80 to 100% by mass, and more preferably about 90 to 100% by mass (particularly, about 95 to 100% by mass). The liquid-retaining layer may contain the solvent-spinning cellulose fiber alone (100% by mass). A liquid-retaining layer containing the solvent-spinning cellulose fiber alone has a particularly excellent transparency in a wet state. In a case where the proportion of the solvent-spinning cellulose fiber is too small, the liquid-retaining layer has an unbalanced transparency and strength under wetting, and thus the resulting sheet is hard to handle as a facial mask.

In particular, in order to control (or adjust) the softness, the liquid-retaining layer may contain the solvent-spinning cellulose fiber and a rayon fiber in combination. In a combination of both fibers, the ratio (mass ratio) of the solvent-spinning cellulose fiber relative to the rayon fiber [the former/the latter] is about 99/1 to 10/90, preferably about 98/2 to 30/70, and more preferably about 97/3 to 50/50 (particularly, about 95/5 to 70/30). In a case where the proportion of the solvent-spinning cellulose fiber is too small, the liquid-retaining layer has a low transparency in a wet state.

The liquid-retaining layer may have a layered structure composed of a plurality of layers with different fiber compositions. For example, when the sheet is used as a sheet for cosmetic preparation impregnation, or the like, an effect that a region at or near a skin-contact side (a side to be contacted with the skin) becomes a wet (or moist) state more rapidly can be expected by increasing the ratio of the hydrophilic fiber in the region at or near the skin-contact side. Specifically, when the laminated sheet comprises the liquid-retaining layer having a layer comprising the hydrophilic fiber in a higher ratio and located in a skin-contact side, and is gently placed on (or laid on) the skin, the liquid component is moved toward the direction that the ratio of the hydrophilic fiber is higher in the liquid-retaining layer and allows the skin-contact side to be a high wet (moist) state in a short time. The liquid-retaining layer may have a two-layer structure, for example, a structure composed of a first layer which is located at a front (or outer) side of the sheet and contains a hydrophilic fiber in a ratio of not more than 30% by mass (e.g., 10 to 30% by mass) and a second layer which is located at a skin-contact side and contains a hydrophilic fiber in a ratio of not less than 70% by mass (e.g., 70 to 90% by mass).

The cross-sectional form of the fiber (the transparent fiber, or the transparent fiber and the opaque fiber) for the liquid-retaining layer is not particularly limited to a specific one. For example, the cross-sectional form may include various cross-sectional forms such as a circular form, a modified (or deformed) form (such as a flat form or an elliptical form), a polygonal form, a multi-leaves form (a 3- to 14-leaves form), a hollow form, a V-shaped form, a T-shaped form, an H-shaped form, an I-shaped form (dog-bone form), and an array form. Among them, a circular cross-sectional form, an elliptical cross-sectional form, or the like is widely used.

The length of the fiber for the liquid-retaining layer is not particularly limited to a specific one. The fiber may be a continuous fiber (a continuous filament). The fiber preferably includes a staple fiber (or a short fiber) because the staple fibers are three-dimensionally entangled with each other to easily express a suitable strength under wetting. The staple fiber may have an average fiber length selected from the range of about 5 to 300 mm (for example, about 10 to 100 mm). In order to obtain a dry nonwoven fabric by a carding process, for example, a fiber having an average fiber length of about 20 to 70 mm, preferably about 25 to 60 mm, and more preferably about 30 to 55 mm, easily forms a web having a uniform fabric appearance in view of easy passage through a card. The average fiber length of the fiber may suitably be adjusted according to purposes.

In view of an excellent balance between the transparency and the liquid retentivity, the fiber for the liquid-retaining layer has a fiber diameter (number-average fiber diameter) of, for example, about 0.1 to 30 µm, preferably about 0.5 to 20 µm, and more preferably about 1 to 15 µm (in particular, about 3 to 13 µm).

The nonwoven fabric (nonwoven structural member) for the liquid-retaining layer has a basis weight of, for example, about 20 to 200 g/m$^2$, preferably about 25 to 150 g/m$^2$, and more preferably about 30 to 120 g/m$^2$ (particularly about 30 to 100 g/m$^2$). Further, in a case where the nonwoven fabric is used as a facial mask, in order to maintain a high transparency in a wet state and a suitable strength in a wet state, the nonwoven fabric may have a basis weight of, for example, about 20 to 60 g/m$^2$, preferably about 30 to 50 g/m$^2$, and more preferably about 35 to 45 g/m$^2$. When the basis weight is excessively small, it is difficult to ensure a space for liquid retention between fibers. Moreover, when the basis weight is excessively large, the quantity of the liquid to be retained in the liquid-retaining layer is excessively increased. As a result, a large quantity of the effective ingredient stays in the liquid-retaining layer without reaching the skin, and the effective ingredient is often wasteful.

The density (apparent density) of the liquid-retaining layer is, for example, about 0.03 to 0.20 g/cm$^3$, preferably about 0.05 to 0.17 g/cm$^3$, and more preferably about 0.08 to 0.15 g/cm$^3$, depending on the viscosity of the liquid component (e.g., a cosmetic preparation) for impregnation. A liquid-retaining layer having an excessively low density makes the liquid retentivity of the sheet low and easily causes dripping of the liquid from the sheet in handling. On the other hand, a liquid-retaining layer having an excessively high density decreases the quantity of the liquid to be retained, and additionally shows a tendency to slow down the movement speed of the liquid to the adhesion layer.

The void ratio of the liquid-retaining layer may for example be not less than 80% (e.g., 80 to 990), preferably not less than 85% (e.g., 85 to 980), and more preferably not less than 90% (e.g., 90 to 95%) in order to ensure the impregnation quantity of the liquid component (e.g., a cosmetic preparation).

The thickness of the liquid-retaining layer may be selected from the range of about 100 to 3000 µm and is, for example, about 200 to 2000 µm, preferably about 300 to 1500 µm, and more preferably about 400 to 1200 µm (particularly about 500 to 1000 µm).

[Process for Producing Liquid-Retaining Layer]

The nonwoven fabric or nonwoven structural member for the liquid-retaining layer can be produced by a conventional method, for example, a spunlace method, a needlepunch method, and a steam jet method. Among these methods, when the cost is considered as important, the spunlace method, by which the nonwoven fabric can be produced industrially at a high speed, may be used. In order to improve the liquid retentivity of the nonwoven fabric by increasing the bulkiness thereof, there may be used the thermal bonding method, the steam jet method, and others (particularly, the steam jet method, in terms of uniform bonding in the thickness direction and highly balanced form retentivity and bulkiness).

For the spunlace method, the staple fibers, for example, plural kinds of transparent fibers, may be blended and opened by, e.g., carding with a carding machine to produce a nonwoven fabric web. The nonwoven fabric web may be a parallel web (in which the fibers are arranged in a forward (or traveling) direction of a carding machine), a cross web (in which the parallel webs are cross-laid), a random web (in which the fibers are randomly arranged), or a semi-random web (which is intermediate between the parallel web and the random web), depending on the species or mixing ratio of the fibers constituting the web. For the random web or the cross web, since the fibers are entangled with each other in the crosswise (or cross-machine) direction of the web to inhibit the stretch of the web in the crosswise direction, these webs have a tendency to decrease the conformity (or clinging property) to the skin in use. Accordingly, the parallel web and the semi-random web, which can ensure the softness and stretch in the crosswise direction of the liquid-retaining sheet, are preferred compared with the random web and the cross web.

Further, for the spunlace method, the resulting nonwoven fabric web is subjected to hydroentangling. In the hydroentangling, a high-pressure water flow spouted (or jetted) from a nozzle plate is led to collide with the nonwoven fabric web placed on a porous supporting member to three-dimensionally entangle the fibers of the nonwoven fabric web with each other and integrate the fibers; in which the nozzle plate has jet orifices drawn up (or arranged) in one to two lines, each orifices having a diameter of about 0.05 to 0.20 mm and a pitch of about 0.30 to 1.50 mm. When the nonwoven fabric web is subjected to the three-dimensional entanglement, it is preferred that the nonwoven fabric web placed on a moving porous supporting member be treated once or a plurality of times with a water flow at a water pressure of about 10 to 150 kg/cm$^2$ ($\approx$1 to 15 MPa), preferably about 20 to 120 kg/cm$^2$ ($\approx$2 to 12 MPa), more preferably about 30 to 100 kg/cm$^2$ ($\approx$3 to 10 MPa). A preferred manner is as follows: the jet orifices are arranged in line in a direction perpendicularly to the traveling direction of the nonwoven fabric web, and the nozzle plate having the jet orifices arranged is vibrated in a direction perpendicular to the traveling direction of the nonwoven fabric web placed on the porous supporting member at the same width as the pitch of the jet orifices to lead the water flow to collide with the nonwoven fabric web uniformly. The porous supporting member for placing the nonwoven fabric web is not particularly limited to a specific one as far as the water flow can pass through the nonwoven fabric web. The porous supporting member may include, for example, a mesh screen (e.g., a wire mesh) and a punched (or perforated) board. The distance between the jet orifices and the nonwoven fabric web may be selected depending on the water pressure and is, for example, about 1 to 10 cm. When the distance is beyond this range, the resulting nonwoven fabric easily deteriorates the fabric appearance or has an insufficient three-dimensional entanglement of the fibers.

The nonwoven fabric web may be subjected to a drying treatment after the hydroentangling. As the drying treatment, first, it is preferred to remove excess water (or moisture) from the hydroentangled nonwoven fabric web. The removal of the excess water can be conducted by a known method. For example, the excess water may be removed using a squeezing machine (such as a mangle (mangle roll)) to a certain extent, and successively the remaining water may be removed using a dryer such as a suction-band type hot-wind circulation dryer.

For the steam jet method, the fibers of the resulting nonwoven fabric web may be entangled with each other by spraying the web with a high-temperature water vapor (high-pressure steam). For the steam jet method, in addition to entanglement of the fibers, the fibers may be thermally bonded under moisture by using a web containing a hydrophilic fiber (a moistenable-thermal adhesive fiber) comprising a moistenable-thermal adhesive resin (such as an ethylene-vinyl alcohol-series copolymer) on at least a surface of the fiber. Specifically, for the steam jet method, when the fiber web transferred by a belt conveyor passes through a high-speed and high-temperature water vapor stream which is jetted or sprayed from a nozzle of a vapor spraying apparatus, the sprayed high temperature water vapor allows the fibers to be entangled with each other. In the presence of the moistenable-thermal adhesive fibers, the fibers (the moistenable-thermal adhesive fibers, or the moistenable-thermal adhesive fiber and the hydrophobic fiber) are three-dimensionally bonded to each other by melt-bond of the moistenable-thermal adhesive fibers uniformly in the thickness direction.

In order to supply the fiber web with a water vapor, a conventional water vapor spraying apparatus is used. The water vapor spraying apparatus may be attached to each of two belt conveyors for holding the web therebetween in order to spray a high-temperature water vapor from the both sides of the fiber web. As an endless belt used for the conveyor, a net having a mesh count larger than about (for example, a net having a mesh count of about 10 to 60) is usually employed.

In order to spray the high-temperature water vapor, a plate or die having a plurality of predetermined orifices successively arranged in one or a plurality of lines in a width direction thereof is used as a nozzle, and the plate or die is disposed to arrange the orifices in the width direction of the fiber web to be conveyed. The orifice has a diameter of, for example, about 0.05 to 2 mm (particularly about 0.1 to 1 mm). The orifice has a pitch of, for example, about 0.5 to 3 mm (particularly about 1 to 2 mm).

The pressure of the high-temperature water vapor is, for example, about 0.1 to 2 MPa, preferably about 0.2 to 1.5 MPa, and more preferably about 0.3 to 1 MPa. The temperature of the high-temperature water vapor is, for example, about 70 to 150° C., preferably about 80 to 120° C., and more preferably about 90 to 110° C. The speed of the treatment with the high-temperature water is, about not more than 200 m/minute, preferably about 1 to 100 m/minute, and more preferably about 1 to 50 m/minute.

[Nonporous Transparent Layer]

The liquid-retaining sheet of the present invention may contain the liquid-retaining layer alone. The liquid-retaining sheet may further contain a nonporous transparent layer formed from a transparent resin. The nonporous transparent layer (outer layer) may be laminated directly or indirectly on a first side of the liquid-retaining layer. Since the nonporous transparent layer is laminated opposite side of the skin-contact side and is nonporous, the contact of the liquid-retaining layer with the skin closes up the liquid component in the liquid-retaining layer and opens up pores in the skin with an increase in temperature. Therefore, the absorption of the effective ingredient can be promoted. Moreover, the nonporous transparent layer can prevent the liquid component from drying and allows supply of the effective ingredient to the skin for a long period of time.

The transparent resin may include the resin components as exemplified in the transparent fiber mentioned above. Among the above-mentioned resin components, a preferred resin in the light of transparency or formability includes a polyolefin-series resin (e.g., a polyethylene and a polypropylene), a polyester-series resin [e.g., a poly(alkylene arylate)-series resin, such as a poly(ethylene terephthalate) or a poly(butylene terephthalate)], a polyamide-series resin (e.g., an aliphatic polyamide, such as a polyamide 6), a polyurethane-series resin (e.g., a polyester-series urethane resin). In the light of easy lamination of the nonporous transparent layer and the liquid-retaining layer, a particularly preferred resin includes polyethylene-series resin (such as a polyethylene).

The nonporous transparent layer may contain a conventional additive similar to the above-mentioned additive of the liquid-retaining layer as far as the transparency is not impaired.

As usage, the nonporous transparent layer may be an oriented film or may be a laminate of plural kinds of transparent layers.

The nonporous transparent layer has a thickness of, for example, about 3 to 200 μm, preferably about 5 to 100 μm, and more preferably about 10 to 50 μm (particularly, about 10 to 30 μm). The thickness ratio of the nonporous transparent layer relative to the liquid-retaining layer [the nonporous transparent layer/the liquid-retaining layer] is about 1/5 to 1/300, preferably about 1/10 to 1/200, and more preferably about 1/20 to 1/150 (particularly, about 1/30 to 1/100). A nonporous transparent layer having an excessively large thickness reduces the softness of the liquid-retaining sheet. A nonporous transparent layer having an excessively small thickness is difficult to form. In addition, the nonporous transparent layer less prevents the liquid component from drying due to small holes (pinholes) appearing in the nonporous transparent layer.

The nonporous transparent layer is not particularly limited to a specific one as far as the layer can be formed into a film having a uniform thickness. As the film-forming method, a conventional method may be used. In the light of productivity or others, a preferred method includes an extrusion molding, an inflation molding, and others.

A means to unite (or join) the nonporous transparent layer and the liquid-retaining layer may include an adhesive. In order to obtain high productivity, transparency, and strong adhesive strength, a preferred method includes an extrusion coating (extrusion lamination) in which a transparent resin in a thermally melt-bondable state is laminated on the liquid-retaining layer by extrusion molding. Further, in a case where a plurality of nonporous transparent layers is laminated, these layers may be thermocompression-bonded with a heating roller. A preferred method includes a heat lamination in which a resin for forming one nonporous transparent layer is prepared in a thermally melt-bondable state and used as a hot melt agent.

[Adhesion Layer]

The liquid-retaining sheet of the present invention may further contain an adhesion layer (contact layer) laminated directly or indirectly on at least one side of the liquid-retaining layer; the adhesion layer contains (or is formed from) a meltblown nonwoven fabric. In particular, in a case where the nonporous transparent layer is formed on or over a first side of the liquid-retaining sheet, the adhesion layer may be laminated on or over a second side of the sheet or may be interposed between the nonporous transparent layer and the liquid-retaining layer.

The adhesion layer, which is laminated to the skin-contact side (the side that contacts with the skin) and is directly contacted with the skin, delivers (or moves or transport) a cosmetic preparation from the liquid-retaining layer to the skin, and it is necessary for the adhesion layer to have a structure suitable for smooth delivery of the liquid component (e.g., a cosmetic preparation). Thus the adhesion layer is a through-porous structure which allows the liquid component to be delivered from the liquid-retaining layer to the skin.

Further, according to the present invention, the adhesion layer (or dense layer) is located at a side directly contacting with the skin, has a soft feel against the skin, adheres to (is contacted with) the skin closely by attaching or laying the adhesion layer on the skin, and delivers the liquid component to the skin through pores while retaining the liquid component fed from the liquid-retaining layer in the voids between the fibers of the adhesion layer or on the fibers. In particular, according to the present invention, the adhesion layer contains a nonwoven fabric (or nonwoven structural member) obtained by a meltblown method or the like, where the fiber of the nonwoven fabric has a uniform and ultrafine fiber diameter. Since such an adhesion layer is a dense layer containing an ultrafine fiber and has a flat and smooth surface, the contact of the fiber with the skin causes very low scratchy irritation. Further, probably because the adhesion layer is a dense layer containing the ultrafine fiber, a liquid coat uniformly spreading at the interface between the adhesion layer and the skin is formed. The liquid coat plays an excellent role in a long-time close contact with (or clinging or adhesion to) the skin.

The nonwoven fabric or nonwoven structural member for the adhesion layer is not particularly limited to specific one as far as the nonwoven fabric or nonwoven structural member is permeable to the liquid component (liquid effective ingredient) while moderately retaining the liquid component. The nonwoven fabric or nonwoven structural member preferably contains a thermoplastic resin fiber. The thermoplastic resin to be used may include, for example, a resin component as exemplified in the paragraph of the transparent fiber. The resin components may be used alone or in combination. Among them, a polyolefin-series resin, a poly(vinyl alcohol)-series resin, a polyester-series resin, a polyamide-series resin, a polyurethane-series resin, a thermoplastic elastomer, and others are preferred. Further, the resin to be widely used as the thermoplastic resin includes a polyolefin-series resin (such as a polyethylene or a polypropylene), an aliphatic polyamide-series resin (such as a polyamide 6), and a poly (alkylene arylate) resin [such as a poly(ethylene terephthalate) or a poly(butylene terephthalate)]. A polypropylene-series resin is easily formed into a sheet-shaped nonwoven fabric having a low basis weight and has an excellent productivity. In these respects, the polypropylene-series resin (such as a polypropylene) is particularly preferred.

The fiber for the adhesion layer preferably has the same purity and coloring agent content as those of the transparent fiber for the liquid-retaining layer. Moreover, the fiber for the adhesion layer may contain the same conventional additives as those described in the liquid-retaining layer.

The cross-sectional form of the fiber for the adhesion layer may be the same as that of the fiber for the liquid-retaining layer, and is usually a circular form, an elliptical form, and others.

In view of the adhesion to the skin, and others, the diameter of the fiber for the adhesion layer is ultrafine, which is smaller than that of the fiber for the liquid-retaining layer. The concrete fiber diameter (number-average fiber diameter) may be about not more than 10 µm. For example, the fiber diameter may be about 0.1 to 9 µm, preferably about 0.5 to 8 µm (e.g., about 1 to 6 µm), more preferably 1 to 7 µm (particularly about 1.5 to 6 µm), and particularly preferably about 2 to 6 µm (e.g., about 2 to 5 µm). When the average fiber diameter is excessively small, the adhesion layer has a low function of moving the liquid component (liquid effective ingredient) (such as a cosmetic preparation) from the liquid-retaining layer toward the skin. Moreover, when the average fiber diameter is excessively large, the adhesion layer impresses as rough against the skin, and in addition, fails to uniformly spread a liquid coat formed at the interface between the adhesion layer and the skin, whereby deteriorating in the adhesive performance.

The fiber for the adhesion layer is an ultrafine fiber and has a uniform fiber diameter. Specifically, the standard deviation of the fiber diameter may be not more than 5, for example, about 0 to 5, preferably about 0 to 4 (e.g., about 0 to 3), and more preferably about 0 to 2.5 (particularly, about 0 to 2). For example, the standard deviation may be about 0.1 to 5, preferably about 0.5 to 3, and more preferably about 1 to 2. Further, the coefficient of fluctuation of the fiber diameter is about not more than 80%, for example, about 0 to 80%, preferably about 0 to 70%, and more preferably about 0 to 65% (particularly, about 0 to 60%). For example, the coefficient of fluctuation may be about 1 to 80%, preferably about 10 to 70%, and more preferably about 20 to 60%. According to the present invention, since the fiber for the adhesion layer is ultrafine and has a uniform diameter as described above, the fiber causes less irritation to the skin and can form a dense and porous structure.

The nonwoven fabric (or nonwoven structural member) for the adhesion layer has a basis weight of, for example, about 3 to 50 g/m$^2$, preferably about 4 to 30 g/m$^2$, and more preferably about 4 to 20 g/m$^2$ (particularly, about 5 to 10 g/m$^2$). When the basis weight of the nonwoven fabric (particularly, a meltblown nonwoven fabric) is excessively small, the fiber of the liquid-retaining layer tends to be exposed on the surface of the adhesion layer. Accordingly, the adhesion layer impresses as rough against the skin, and in addition, fails to uniformly spread a liquid coat formed at the interface between the adhesion layer and the skin, whereby deteriorating in the adhesive performance. When the basis weight of the nonwoven fabric is excessively large, the adhesion layer has a low function of moving the liquid effective ingredient (such as a cosmetic preparation) from the liquid-retaining layer toward the skin.

The density of the adhesion layer (the apparent density of the adhesion layer in the liquid-retaining sheet) is, for example, about 0.05 to 0.35 g/cm$^3$, preferably about 0.08 to 0.25 g/cm$^3$, and more preferably about 0.1 to 0.2 g/cm$^3$. When the density of the adhesion layer is excessively low, there is not enough amount of the fiber to form the adhesion layer, and it is difficult to form a uniform ultrafine-fiber layer as the adhesion layer. In contrast, when the density of the adhesion layer is excessively high, the adhesion layer has a low function of moving the liquid effective ingredient (such as a cosmetic preparation) from the liquid-retaining layer toward the skin.

The void ratio of the adhesion layer (the void ratio of the adhesion layer in the liquid-retaining sheet) may be not less than 70% (e.g., about 70 to 99%), preferably not less than 75% (e.g., about 75 to 950), and more preferably not less than 80% (e.g., about 80 to 90%) in order to uniformly move the liquid effective ingredient (e.g., a cosmetic preparation) fed from the liquid-retaining layer toward the skin in a short time.

The thickness of the meltblown nonwoven fabric for the adhesion layer may be selected from the range of about 10 to 500 jam and is, for example, about 30 to 500 µm, preferably about 30 to 200 µm, and more preferably about 35 to 150 µm (particularly, about 40 to 100 µm). When the thickness of the adhesion layer is excessively small, there is not enough amount of the fiber to form the adhesion layer, and it is difficult to form a uniform ultrafine-fiber layer as the adhesion layer. In contrast, when the thickness of the adhesion layer is excessively large, the adhesion layer has a low function of moving the liquid component from the liquid-retaining layer toward the skin.

The thickness ratio of the adhesion layer relative to the liquid-retaining layer [the adhesion layer/the liquid-retaining layer] is about 1/4 to 1/100, preferably about 1/5 to 1/80, and more preferably about 1/6 to 1/50 (particularly, about 1/7 to 1/30). By increasing the thickness ratio of the liquid-retaining layer, the liquid-retaining layer can be brought close to the skin, and additionally a larger portion of the liquid-containing sheet has a space suitable for liquid retention as a sheet to be impregnated with the liquid component (e.g., a cosmetic preparation).

As a method for producing the adhesion layer and a method for uniting (or joining) the adhesion layer to the liquid-retaining layer, there may be used a method described in International Publication WO2011/004834 (Patent Document 3), or others.

[Liquid-Retaining Sheet]

The liquid-retaining sheet of the present invention contains (or is formed from) at least the liquid-retaining layer. The liquid-retaining sheet is highly transparent in a wet state and has a transparency shown below of not more than 0.27.

Transparency=Whiteness (%) of a sheet impregnated with 700% by mass of water relative to the sheet mass/Basis weight (g/m$^2$)

The transparency may be about 0.01 to 0.27, and is, for example, about 0.02 to 0.25, preferably about 0.03 to 0.2, and more preferably about 0.05 to 0.15 (particularly, about 0.06 to 0.1).

The liquid-retaining sheet of the present invention may have a whiteness of not more than 35% when the sheet is impregnated with 700% by mass of water relative to the sheet mass. For example, the whiteness may be about 1 to 35%, preferably about 3 to 30%, and more preferably about 5 to 25% (particularly, about 8 to 20%). In a case where the liquid-retaining sheet requires a high transparency suitable for a facial mask, the above whiteness may be about 1 to 15%, for example, about 1 to 10%, preferably about 1.5 to 8%, and more preferably about 2 to 5% (particularly, about 2 to 4%). According to the present invention, the transparency necessary for the liquid-retaining sheet (in particular, a facial mask) can be evaluated based on this whiteness.

In a case where the transparency and the whiteness are too large, the liquid-retaining sheet has a low transparency in a wet state. Incidentally, in the present invention, detailed methods of measuring the whiteness and the transparency are described in the after-mentioned Examples.

The liquid-retaining sheet of the present invention may be a sheet in which the liquid-retaining layer is impregnated (or soaked) with a liquid component, for example, a skin care sheet (in particular, a facial mask) in which the liquid-retaining layer is impregnated with a liquid component containing a cosmetic preparation.

The liquid-retaining sheet of the present invention may have a basis weight selected from the range of about not more than 200 g/m$^2$, for example, a basis weight of about 20 to 180 g/m$^2$, preferably about 23 to 150 g/m$^2$ (e.g., about 30 to 120 g/m$^2$), more preferably about 35 to 100 g/m$^2$ (particularly, about 50 to 90 g/m$^2$). A too large basis weight causes a low transparency in a wet state.

The liquid-retaining sheet of the present invention also has a reasonable strength under wetting due to suitable entanglement of the staple fibers with each other so that the sheet can closely adhere to the skin (e.g., the face) for easy attachment to the skin. The sheet has a stress at 30% elongation under wetting in accordance with JIS L 1913, for example, of not less than 1.5 N/5 cm (for example, 1.5 to 10 N/5 cm) in at least one direction; the stress at 30% elongation is, for example, about 1.8 to 8 N/5 cm, preferably about 2 to 7 N/5 cm (e.g., about 2.5 to 6 N/5 cm), and more preferably about 3 to 5 N/5 cm (in particular, about 3.5 to 4.5 N/5 cm) in at least one direction. A liquid-retaining sheet having a stress at elongation within this range allows improvement in handling as a facial mask. A liquid-retaining sheet having an excessively small stress at elongation is overstretched when attached to the skin (such as the face), and it is difficult to handle the sheet. A liquid-retaining sheet having an excessively large stress at elongation has a low adhesion to the skin. Incidentally, the stress at 30% elongation under wetting can be measured by a method detailed in Examples described below.

The liquid-retaining sheet of the present invention can also be used as an application for absorbing a liquid component, for example, a surface material for a sanitary napkin or a diaper, and a sheet for body fluid absorption (or a skin-washing sheet) such as a diaper liner or a wet wipe (or a pre-moistened wipe). Since the liquid-retaining sheet has a well-balanced liquid retentivity and liquid releasability, is transparent under wetting and is easy to closely adhere to the skin, it is preferred to be used for an application in which the sheet is impregnated with a liquid component (such as a beauty component or a medicinal component) and closely adheres to the skin. Examples of the application may include various skin care sheets such as a facial mask (facial mask sheet), a makeup-removing sheet or a cleansing sheet, a body-washing sheet (e.g., a sweat-wiping sheet and an oil-blocking (or oil-absorbing) sheet), a cooling sheet, and a medicated or therapeutic sheet (e.g., an itching-controlling (or antipruritic) sheet and a wet compress).

The skin care sheet of the present invention may be a sheet which is impregnated with these liquid components in use, or a sheet which is previously impregnated with the liquid component (what is called a wet sheet).

According to the present invention, the liquid component may include a liquid substance (such as a solvent or a liquid oil), and in addition, a solution or a dispersion (e.g., a cosmetic preparation and a milky lotion) which contains the effective ingredient (such as a beauty component or a medicinal (efficacious) component) in the liquid substance. The solvent may be a lipophilic solvent. In terms of the safety for the human body, a hydrophilic solvent is preferred. The hydrophilic solvent may include, for example, water, a lower aliphatic alcohol (e.g., a $C_{1-4}$alkyl alcohol such as ethanol or isopropanol), and an alkylene glycol (e.g., ethylene glycol, diethylene glycol, and propylene glycol). These hydrophilic solvents may be used alone or in combination. The liquid oil may include, for example, an unsaturated higher fatty acid (e.g., oleic acid and oleyl alcohol), an oil derived from animals or plants (e.g., a jojoba oil, an olive oil, a palm oil, a camellia oil, a macadamia nut oil, an avocado oil, a corn oil, a sesame oil, a wheat germ oil, a flaxseed oil, a castor oil, and squalane), a mineral oil (e.g., a liquid paraffin (or petrolatum), a polybutene, and a silicone oil), and a synthetic oil (e.g., a synthetic ester oil and a synthetic polyether oil). These liquid oils may be used alone or in combination.

These liquid substances may be used alone or in combination. For example, the liquid oil may be used as an additive (oil content) in combination with the hydrophilic solvent (such as water or ethanol). Among these liquid substances, usually, water, a lower alcohol or a mixture thereof is employed. Preferably, water and/or ethanol (particularly, water) is used. For example, for the combination use of water with the lower alcohol (particularly, ethanol), the ratio (volume ratio) of water relative to the lower alcohol [the water/the lower alcohol] may be about 100/0 to 30/70, preferably about 100/0 to 50/50, more preferably about 100/0 to 70/30, and, e.g., about 99/1 to 80/20.

The effective ingredient (or component) may include a conventional additive, for example, a physiologically active component (e.g., a skin-softening agent, a skin-whitening agent, an antiperspirant, a skin-barrier agent, an anti-inflammatory agent, an agent for controlling skin itching (or an antipruritic), a blood-circulation-promoting agent, and a cell-activator), a moisturizing agent, an emollient agent, a cleansing agent, an ultraviolet absorber, a surfactant, an astringent agent, an enzyme, an algefacient, a germicide or an antibacterial agent, an antioxidant, an amino acid, a cooling agent, a perfume, and a coloring agent. These additives may be used alone or in combination. Among these additives, for the skin care sheet, for example, a moisturizing agent, an ultraviolet absorber, a surfactant, an algefacient, an enzyme, an astringent agent, and a germicide or an antibacterial agent, are widely used. In particular, for the facial mask (facial pack) or the cleansing sheet, a moisturizing agent or an emollient agent may be added to a hydrophilic solvent. The moisturizing agent or the emollient agent may include, for example, dipropylene glycol, 1,3-butylene glycol, a polyethylene glycol, a polyoxyethylene-polyoxypropylene block copolymer, a polyoxyethylene sorbitan fatty acid ester, a polyoxyethylene sucrose fatty acid ester, glycerin, sodium hyaluronate, a polyoxymethyl glycoside, a poly(vinyl alcohol), a polyvinylpyrrolidone, and a water-soluble cellulose ether (e.g., a methyl cellulose, a hydroxyethyl cellulose, a hydroxypropyl cellulose, a hydroxyethylmethyl cellulose, and a hydroxypropylmethyl cellulose). The total proportion of the moisturizing agent and the emollient agent is, for example, about 0.1 to 50% by mass, preferably about 1 to 30% by mass, and more preferably about 5 to 20% by mass in the solution.

The proportions of these additives may suitably be selected according to the purposes. For example, the proportion of the liquid substance (such as water or ethanol) is usually about 30 to 99% by mass, preferably about 40 to 95% by mass, and more preferably about 50 to 90% by mass in the total liquid component containing the additive(s).

Since the liquid-retaining sheet of the present invention is transparent in a wet state and can closely adhere to the skin easily, the liquid-retaining sheet is particularly suitable for a sheet to be fixed on the skin (such as a facial mask or a wet compress). For example, since the liquid-retaining sheet is transparent in a wet state, an area separated from the skin without close adhesion to the skin can easily be found and suitably adhere to the skin. Thus the sheet can be conformed to the fine (or small) curvature or gap of the skin (e.g., the root of the nose) without leaving space. Thus, the effective ingredient of the facial mask can effectively infiltrate in the skin.

The liquid-retaining sheet of the present invention is also suitable for a cleansing sheet or a skin-washing sheet, and the like. Specifically, since the liquid-retaining sheet of the present invention can be conformed to the fine (or small) curvature or gap of the face without leaving space, the sheet can effectively remove a makeup (e.g., a makeup cosmetic preparation such as a foundation, a face powder, a lipstick, or an eye makeup) from the skin.

Thus, when the liquid-retaining sheet of the present invention is used as a living-body application sheet for liquid impregnation (e.g., a facial mask and a cleansing sheet), usually the liquid-retaining sheet is impregnated with the liquid component and then applied to or contacted with the skin of a living body.

EXAMPLES

Hereinafter, the following examples are intended to describe this invention in further detail and should by no means be interpreted as defining the scope of the invention. Incidentally, each of physical properties in Examples and Comparative Examples was determined or evaluated as follows. Moreover, details of fibers and films used in the following Examples and Comparative Examples are described as below.

[Basis Weight (g/m$^2$)]

In accordance with JIS L 1906, a sample was allowed to stand for 24 hours in a standard state (a temperature of 20° C. and a humidity of 65%) and then a specimen having a width of 1 m and a length of 1 m was obtained from the sample, and the weight (g) of the specimen was scaled. The measured value (g) was rounded off to the closest whole number, and the calculated value was taken as a basis weight.

[Thickness (μm)]

A sample was cut along (or parallel to) an MD direction in a direction perpendicular to a sample surface thereof with a razor (manufactured by FEATHER Safety Razor Co., Ltd., "Feather Razor S, single-edged"). The cut surface (or cross-sectional surface) of the specimen was observed with a digital microscope [manufactured by KEYENCE Corporation, DIGITAL MICROSCOPE VHX-900] and the thickness of the specimen was measured.

[Density (g/cm$^3$)]

The basis weight (g/m$^2$) was divided by the thickness to determine the density.

[Void Ratio (%)]

The void ratio was calculated using the following equation based on the weight (g) of the nonwoven fabric, the specific gravity of the fiber (g/cm$^3$), the apparent volume of the nonwoven fabric (cm$^3$). Incidentally, the apparent volume of the nonwoven fabric was calculated by multiplication of the area of the sheet surface of the nonwoven fabric and the value (as height) obtained through the measurement of the thickness.

$$\text{Void ratio (\%)}=100-[(\text{weight}\times100)/(\text{specific gravity of fiber}\times\text{apparent volume of nonwoven fabric})]$$

[Average Fiber Diameter (μm)]

A fiber sheet was cut into a test piece (length×width=5 cm×5 cm), and a micrograph of the central region (a region with center at the intersection of the diagonals) of the surface of the test piece was taken using a scanning electron microscope (SEM) with 1000 magnifications. A circle with radius 30 cm and center at the central region (the intersection of the diagonals) of the obtained micrograph was drawn on the micrograph, and 100 fibers were randomly selected from the inside of the circle. Each fiber diameter at the central region or a neighborhood thereof in the length direction was measured with vernier calipers, and the average value was taken as an average fiber diameter (number-average fiber diameter). Incidentally, the fiber diameters of all fibers shown in the micrograph were determined without distinction between a fiber located on the surface of the fiber sheet and a fiber located in the inside of the fiber sheet.

[Whiteness and Transparency]

The whiteness and the transparency were measured according to the following procedure.

(1) cut a measuring sample into a size of 10×10 cm to give a test piece, weigh the test piece, and measure the thickness of the test piece, (2) measure a whiteness (WI value) of a black acrylic board (a methacrylic resin extrusion board, "COMOGLAS" manufactured by KURARAY CO., LTD., 12.5 cm×12.5 cm, thickness: 3 mm) by a color-difference meter ("Chroma meter CR-410" manufactured by KONICA MINOLTA, INC.), (3) place the test piece on the black acrylic board used in the step (2) and measure a whiteness (WI value) by a color-difference meter, (4) impregnate the test piece with ion-exchange water with a spray to adjust the water content of the test piece to 700%, (5) hold the test piece with a hand roller (width: 4 cm, weight: 280 g, linear load: 70 g/cm), and bring the test piece into close contact with the black acrylic board while pulling out air remaining between the test piece and the black acrylic board, and (6) measure a whiteness (WI value) of the test piece closely adhering to the black acrylic board in a wet state by a color-difference meter.

Based on the resulting whiteness (WI value), the transparency was calculated according to the following equation.

Transparency=Whiteness (%) of a sheet impregnated with 700% by mass of water relative to the sheet mass/Basis weight (g/m²)

Incidentally, the whiteness (%) of a sheet impregnated with 700% by mass of water relative to the sheet mass is given by a difference ($W_1-W_0$), where $W_0$ represents a WI value of the black acrylic board, and $W_1$ represents a WI value of the test piece impregnated with 700% by mass of ion-exchange water and closely adhering to the black acrylic board. $W_0$ was 6.67.

[Stress at Elongation Under Wetting]

In accordance with a method described in JIS L 1913 (Nonwoven fabric made of staple fibers) 6.3.2 (Tensile strength and elongation percentage tests under wetting), the stress at elongation under wetting was measured. Specifically, the sample was put in water at 20° C.±2° C. and then the sample was left until the sample sank under gravitation, or the sample was submerged in water for not less than one hour; and thereafter the sample was taken out of the water, and immediately the stress at 30% elongation was measured in the cross direction (CD) of the nonwoven fabric using a constant-rate-of-extension type tensile testing machine (manufactured by Shimadzu Corporation).

[Fiber of Liquid-Retaining Layer]

(Transparent Fiber)

Tencel bright: a Tencel fiber, "TENCEL" manufactured by LENZING, fineness: 1.7 dtex (average fiber diameter: 12 μm)×average fiber length: 38 mm, titanium oxide content: 0.00% by mass, water retention of nonwoven fabric having basis weight of 50 g/m²: 1183%

Rayon bright: a rayon fiber, "CORONA BH" manufactured by Daiwabo Rayon CO., Ltd., fineness: 1.7 dtex (average fiber diameter: 12 μm)×average fiber length: 44 mm, titanium oxide content: 0.00% by mass Polyester bright: a poly(ethylene terephthalate) (PET) fiber, fineness: 1.56 dtex (average fiber diameter: 11.4 μm)× average fiber length: 51 mm, titanium oxide content: 0.09% by mass T-shaped polyester bright: T-shaped PET, a PET fiber having a T-shaped cross-sectional form, fineness: 2.2 dtex (average fiber diameter: 14 μm)×average fiber length: 51 mm, titanium oxide content: 0.09% by mass Sophista bright: a sheath-core structure conjugated fiber having a core composed of a poly(ethylene terephthalate) and a sheath composed of an ethylene-vinyl alcohol copolymer (EVOH), "SOPHISTA" manufactured by KURARAY CO., LTD., average fiber diameter: 2.2 dtex (average fiber diameter: 13.5 μm)×average fiber length: 51 mm, titanium oxide content of core: 0.05% by mass (Opaque Fiber)

Tencel dull: a Tencel fiber, "LENZING Lyocell" manufactured by LENZING, fineness: 1.7 dtex (average fiber diameter: 12 μm)×average fiber length: 38 mm, titanium oxide content: 0.75% by mass Rayon dull: a rayon fiber, fineness: 1.7 dtex (average fiber diameter: 12 μm)×average fiber length: 38 mm, titanium oxide content: 0.60% by mass Polyester semi dull: a PET fiber, fineness: 1.56 dtex (average fiber diameter: 11.4 μm)×average fiber length: 51 mm, titanium oxide content: 0.50% by mass Sophista semi dull: a sheath-core structure conjugated fiber having a core composed of a poly(ethylene terephthalate) and a sheath composed of an ethylene-vinyl alcohol copolymer (EVOH), "SOPHISTA" manufactured by KURARAY CO., LTD., average fiber diameter: 2.2 dtex (average fiber diameter: 13.5 μm)×average fiber length: 51 mm, titanium oxide content of core: 0.50% by mass Large-fineness rayon dull: a rayon fiber, fineness: 5.5 dtex (average fiber diameter: 21.3 μm)×average fiber length: 51 mm, titanium oxide content: 0.60% by mass

[Fiber of Adhesion Layer]

PP-MB: a polypropylene having an MFR (230° C., 2.16 kg) of 1100 g/10 minutes

Ny-MB: a polyamide 6 having an MFR (230° C., 2.16 kg) of 45 g/10 minutes

[Film of Nonporous Transparent Layer]

PE lami: a low-density polyethylene film (polyethylene: "LD polyethylene Nipolon" manufactured by TOSOH CORPORATION), thickness: 15 μm PET film: a PET film ("LUMIRROR PX52" manufactured by Toray Industries, Inc.), thickness: 12 μm Example 1

Tencel (bright) fiber (100 parts by mass) was opened uniformly, and then a semi-random card web having a basis weight of 100 g/m² was produced in the usual manner. The card web was placed on a punching drum support having an open area ratio of 25% and a hole diameter of 0.3 mm. The card web was continuously moved at a speed of 10 m/minute in a longitudinal direction thereof, and simultaneously subjected to a high-pressure water flow jet from above for entangling treatment to give an entangled fiber web (nonwoven fabric). In the entangling treatment, two nozzles (first and second nozzles) were used; where each nozzle had orifices arranged at an interval of 0.6 mm along the width direction (cross direction) of the web, each orifice had a hole diameter of 0.10 mm, and the distance between these nozzles were 20 cm. The water pressure of the high-pressure water flow jetted from the first nozzle (upstream side) was 2.0 MPa, and that from the second nozzle (downstream side) was 3.0 MPa. The web was placed on an entirely flat support having a finer mesh, and continuously moved, and simultaneously subjected to a high-pressure water flow jet for entangling treatment. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 4.0 MPa. Further, the resulting member was dried at 130° C. to give a liquid-retaining sheet composed of a spunlace nonwoven fabric having a basis weight of 100 g/m².

Examples 2 to 6

For each Example, a liquid-retaining sheet was obtained in the same manner as in Example 1 except that a semi-random card web having a basis weight shown in Table 1 was produced.

Examples 7 to 9

For each Example, a liquid-retaining sheet was obtained in the same manner as in Example 4 except that Tencel (bright) fiber and Rayon (bright) fiber were uniformly blended instead of the Tencel (bright) fiber alone at a ratio shown in Table 1 to give a semi-random card web.

Example 10

A liquid-retaining sheet was obtained in the same manner as in Example 4 except that Rayon (bright) fiber was used instead of Tencel (bright) fiber to give a semi-random card web.

Example 11

A liquid-retaining sheet was obtained in the same manner as in Example 4 except that Sophista (bright) fiber was used instead of Tencel (bright) fiber to give a semi-random card web.

Example 12

A liquid-retaining sheet was obtained in the same manner as in Example 4 except that Polyester (bright) fiber was used instead of Tencel (bright) fiber to give a semi-random card web.

Examples 13 to 14

For each Example, a liquid-retaining sheet was obtained in the same manner as in Example 10 except that a semi-random card web having a basis weight shown in Table 2 was produced.

Example 15

A liquid-retaining sheet was obtained in the same manner as in Example 8 except that a semi-random card web having a basis weight shown in Table 3 was produced.

Example 16

A liquid-retaining sheet was obtained in the same manner as in Example 1 except that 50 parts by mass of Tencel (bright) fiber and 50 parts by mass of Sophista (bright) fiber were uniformly blended instead of 100 parts by mass of Tencel (bright) fiber and that a semi-random card web having a basis weight of 50 g/m² was produced.

Example 17

A liquid-retaining sheet was obtained in the same manner as in Example 1 except that 50 parts by mass of Tencel (bright) fiber and 50 parts by mass of polyester (bright) fiber were uniformly blended instead of 100 parts by mass of Tencel (bright) fiber, that the water pressure of the high-pressure water flow jet in the second entangling treatment was 3.0 MPa, and that a semi-random card web having a basis weight of 70 g/m² was produced.

Example 18

A liquid-retaining sheet was obtained in the same manner as in Example 1 except that 30 parts by mass of Tencel (bright) fiber, 50 parts by mass of Polyester (bright) fiber and 20 parts by mass of Polyester (semi dull) fiber were uniformly blended instead of 100 parts by mass of Tencel (bright) fiber and that a semi-random card web having a basis weight of 52 g/m² was produced.

Examples 19 to 20

For each Example, a liquid-retaining sheet obtained in the same manner as in Example 4 except that Tencel (bright) fiber and Tencel (dull) fiber were uniformly blended instead of Tencel (bright) fiber alone at a ratio shown in Table 3 to give a semi-random card web.

Example 21

Using a general meltblown production equipment, 100 parts by mass of the polyamide resin (MFR=45 g/10 minutes) was spun by a meltblown method at a spinning temperature of 280° C., an air temperature of 280° C., an air pressure of 0.4 MPa, a hole diameter of 0.3 mmφ, a discharged amount of 0.3 g/hole·min., a speed of 19 m/minute, the number of spinning holes in mouthpiece of 400 (arranged in a line), and the resulting fiber was collected on a rotating net conveyor as a support to produce a meltblown nonwoven fabric sheet having a basis weight of 10 g/m², and the sheet was rolled up.

Fifty (50) parts by mass of Tencel (bright) fiber, 30 parts by mass of Polyester (bright) fiber, and 20 parts by mass of T-shaped polyester (bright) fiber were blended uniformly, and then a semi-random card web having a basis weight of 71 g/m² was produced in the usual manner. The card web was placed on a punching drum support having an open area ratio of 25% and a hole diameter of 0.3 mm. The card web was continuously moved at a speed of 50 m/minute in a longitudinal direction thereof, and simultaneously subjected to a high-pressure water flow jet from above for entangling treatment to give an entangled fiber web (nonwoven fabric). In the entangling treatment, two nozzles (first and second nozzles) were used; where each nozzle had orifices arranged at an interval of 0.6 mm along the width direction (cross direction) of the web, each orifice had a hole diameter of 0.10 mm, and the distance between these nozzles were 20 cm. The water pressure of the high-pressure water flow jetted from the first nozzle (upstream side) was 3.0 MPa, and that from the second nozzle (downstream side) was 4.0 MPa. The previously produced meltblown nonwoven fabric sheet having a basis weight of 10 g/m² was unwound with a unwinding apparatus, and superposed on the web. The sheet and the web were placed on an entirely flat support having a finer mesh, and continuously moved, and simultaneously subjected to a high-pressure water flow jet for entangling treatment to entangle fibers constituting the two nonwoven fabrics and give combine these fabrics with each other. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 5 MPa. Further, the resulting member was dried at 120° C. to give a liquid-retaining sheet having a basis weight of 81 g/m².

Example 22

A spunlace nonwoven fabric was produced in the same manner as in Example 1 except that the basis weight was changed to 70 g/m². The spunlace nonwoven fabric was extrusion-coated with a polyethylene film using a T-die extruder to give a liquid-retaining sheet.

Example 23

Using a general meltblown production equipment, 100 parts by mass of the polypropylene resin (MFR=1100 g/10 minutes) was spun by a meltblown method at a spinning temperature of 260° C., an air temperature of 270° C., an air pressure of 0.4 MPa, a hole diameter of 0.3 mmφ, a discharged amount of 0.2 g/hole·min., the number of spinning holes in mouthpiece of 400 (arranged in a line), and the resulting fiber was collected on a net conveyor as a support rotating at a speed of 50 m/minute to produce a meltblown nonwoven fabric sheet having a basis weight of 5 g/m$^2$, and the sheet was rolled up.

Sophista (bright) fiber (100 parts by mass) was opened uniformly, and then a semi-random card web having a basis weight of 70 g/m$^2$ was produced in the usual manner. The card web was placed on a punching drum support having an open area ratio of 25% and a hole diameter of 0.3 mm. The card web was continuously moved at a speed of 50 m/minute in a longitudinal direction thereof, and simultaneously subjected to a high-pressure water flow jet from above for entangling treatment to give an entangled fiber web (nonwoven fabric). In the entangling treatment, two nozzles (first and second nozzles) were used; where each nozzle had orifices arranged at an interval of 0.6 mm along the width direction (cross direction) of the web, each orifice had a hole diameter of 0.10 mm, and the distance between these nozzles were 20 cm. The water pressure of the high-pressure water flow jetted from the first nozzle (upstream side) was 3.0 MPa, and that from the second nozzle (downstream side) was 4.0 MPa. The previously produced meltblown nonwoven fabric sheet having a basis weight of 5 g/m$^2$ was unwound with a unwinding apparatus, and superposed on the web. The sheet and the web were placed on an entirely flat support having a finer mesh, and continuously moved, and simultaneously subjected to a high-pressure water flow jet for entangling treatment to entangle fibers constituting the two nonwoven fabrics and give combine these fabrics with each other. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 5 MPa. Further, the resulting member was dried at 120° C. to give a liquid-retaining sheet having a basis weight of 75 g/m$^2$.

Comparative Example 1

A liquid-retaining sheet was obtained in the same manner as in Example 1 except that Tencel (dull) fiber was used instead of Tencel (bright) fiber to give a semi-random card web having a basis weight of 91 g/m$^2$.

Comparative Example 2

A liquid-retaining sheet was obtained in the same manner as in Example 1 except that Rayon (dull) fiber was used instead of Tencel (bright) fiber to give a semi-random card web having a basis weight of 70 g/m$^2$.

Comparative Example 3

A liquid-retaining sheet was obtained in the same manner as in Example 1 except that 50 parts by mass of Rayon (bright) fiber and 50 parts by mass of Rayon (dull) fiber was uniformly blended instead of 100 parts by mass of Tencel (bright) fiber and that a semi-random card web having a basis weight of 90 g/m$^2$ was produced.

Comparative Example 4

A liquid-retaining sheet was obtained in the same manner as in Example 1 except that Polyester (semi dull) fiber was used instead of Tencel (bright) fiber to give a semi-random card web having a basis weight of 90 g/m$^2$.

Comparative Example 5

A liquid-retaining sheet was obtained in the same manner as in Example 1 except that 30 parts by mass of Tencel (dull) fiber, 50 parts by mass of Rayon (dull) fiber and 20 parts by mass of Semi dull PET fiber were uniformly blended instead of 100 parts by mass of Tencel (bright) fiber and that a semi-random card web having a basis weight of 70 g/m$^2$ was produced.

Comparative Example 6

A liquid-retaining sheet was obtained in the same manner as in Example 1 except that Large fineness rayon (dull) fiber was used instead of Tencel (bright) fiber to give a semi-random card web having a basis weight of 50 g/m$^2$.

Comparative Example 7

A liquid-retaining sheet was obtained in the same manner as in Example 1 except that Sophista (semi dull) fiber was used instead of Tencel (bright) fiber to give a semi-random card web having a basis weight of 70 g/m$^2$.

Comparative Example 8

A liquid-retaining sheet was obtained in the same manner as in Example 1 except that Tencel (dull) fiber was used instead of Tencel (bright) fiber to give a semi-random card web having a basis weight of 30 g/m$^2$.

Comparative Example 9

A liquid-retaining sheet was obtained in the same manner as in Example 1 except that Polyester (semi dull) fiber was used instead of Tencel (bright) fiber to give a semi-random card web having a basis weight of 30 g/m$^2$.

Comparative Example 10

A commercially available cotton nonwoven fabric ("BEMCOT M-3II" manufactured by Asahi Kasei Fibers Corp., water retention of nonwoven fabric having basis weight of 50 g/m$^2$: 843%) was used.

Comparative Example 11

A commercially available cotton nonwoven fabric ("BEMCOT J-CLOTH 300" manufactured by Asahi Kasei Fibers Corp.) was used.

Reference Example 1

A liquid-retaining sheet was obtained in the same manner as in Example 1 except that the basis weight was changed to 202 g/m$^2$.

The evaluation results of the liquid-retaining sheets obtained in Examples 1 to 23, Comparative Examples 1 to 11 and Reference Example 1 are shown in Tables 1 to 5.

TABLE 1

|  |  |  | \multicolumn{9}{c}{Examples} |
| --- | --- | --- | --- | --- | --- | --- | --- | --- | --- | --- | --- |
|  |  |  | 1 | 2 | 3 | 4 | 5 | 6 | 7 | 8 | 9 |
| Liquid-retaining layer (%) | Transparent fiber | Tencel bright | 100 | 100 | 100 | 100 | 100 | 100 | 90 | 50 | 10 |
|  |  | Rayon bright | — | — | — | — | — | — | 10 | 50 | 90 |
|  |  | Polyester bright | — | — | — | — | — | — | — | — | — |
|  |  | T-shaped polyester bright | — | — | — | — | — | — | — | — | — |
|  |  | Sophista bright | — | — | — | — | — | — | — | — | — |
|  | Opaque fiber | Tencel dull | — | — | — | — | — | — | — | — | — |
|  |  | Rayon dull | — | — | — | — | — | — | — | — | — |
|  |  | Polyester semi dull | — | — | — | — | — | — | — | — | — |
|  |  | Sophista semi dull | — | — | — | — | — | — | — | — | — |
|  |  | Large-fineness rayon dull | — | — | — | — | — | — | — | — | — |
|  |  | Basis weight (g/m$^2$) | 100 | 90 | 70 | 50 | 40 | 30 | 50 | 50 | 50 |
| Adhesion layer |  | PP-MB (g/m$^2$) | — | — | — | — | — | — | — | — | — |
|  |  | Ny-MB (g/m$^2$) | — | — | — | — | — | — | — | — | — |
| Transparent layer |  | PE lami (g/m$^2$) | — | — | — | — | — | — | — | — | — |
|  |  | PET film (g/m$^2$) | — | — | — | — | — | — | — | — | — |
|  |  | Basis weight (g/m$^2$) | 100 | 90 | 70 | 50 | 40 | 30 | 50 | 50 | 50 |
|  |  | Thickness (μm/sheet) | 900 | 880 | 820 | 600 | 550 | 310 | 620 | 620 | 620 |
|  |  | Density (g/cm$^3$) | 0.11 | 0.10 | 0.09 | 0.08 | 0.07 | 0.10 | 0.08 | 0.08 | 0.08 |
|  |  | Void ratio (%) | 93 | 93 | 94 | 94 | 95 | 94 | 95 | 95 | 95 |
|  |  | $W_1$ (%) | 14.8 | 13.7 | 12.0 | 10.4 | 9.67 | 8.83 | 11.4 | 15.0 | 17.8 |
|  |  | $W_1 - W_0$ (%) | 8.1 | 7.0 | 5.3 | 3.8 | 3.0 | 2.2 | 4.7 | 8.3 | 11.1 |
|  |  | Transparency | 0.081 | 0.078 | 0.076 | 0.075 | 0.075 | 0.072 | 0.094 | 0.167 | 0.222 |
|  |  | Stress at 30% elongation under wetting (CD) (N/5 cm) | 6.9 | 6.5 | 4.6 | 4.5 | 4.0 | 1.9 | 4.3 | 3.4 | 2.9 |

TABLE 2

|  |  |  | \multicolumn{5}{c}{Examples} |
| --- | --- | --- | --- | --- | --- | --- | --- |
|  |  |  | 10 | 11 | 12 | 13 | 14 |
| Liquid-retaining layer (%) | Transparent fiber | Tencel bright | — | — | — | — | — |
|  |  | Rayon bright | 100 | — | — | 100 | 100 |
|  |  | Polyester bright | — | — | 100 | — | — |
|  |  | T-shaped polyester bright | — | — | — | — | — |
|  |  | Sophista bright | — | 100 | — | — | — |
|  | Opaque fiber | Tencel dull | — | — | — | — | — |
|  |  | Rayon dull | — | — | — | — | — |
|  |  | Polyester semi dull | — | — | — | — | — |
|  |  | Sophista semi dull | — | — | — | — | — |
|  |  | Large-fineness rayon dull | — | — | — | — | — |
|  |  | Basis weight (g/m$^2$) | 50 | 50 | 50 | 70 | 30 |
| Adhesion layer |  | PP-MB (g/m$^2$) | — | — | — | — | — |
|  |  | Ny-MB (g/m$^2$) | — | — | — | — | — |
| Transparent layer |  | PE lami (g/m$^2$) | — | — | — | — | — |
|  |  | PET film (g/m$^2$) | — | — | — | — | — |
|  |  | Basis weight (g/m$^2$) | 50 | 50 | 50 | 70 | 30 |
|  |  | Thickness (μm/sheet) | 620 | 880 | 670 | 660 | 330 |
|  |  | Density (g/cm$^3$) | 0.08 | 0.06 | 0.07 | 0.11 | 0.09 |
|  |  | Void ratio (%) | 95 | 96 | 95 | 93 | 94 |
|  |  | $W_1$ (%) | 17.7 | 10.6 | 19.2 | 23.1 | 13.3 |
|  |  | $W_1 - W_0$ (%) | 11.0 | 3.9 | 12.5 | 16.4 | 6.6 |
|  |  | Transparency | 0.220 | 0.078 | 0.251 | 0.234 | 0.220 |
|  |  | Stress at 30% elongation under wetting (CD) (N/5 cm) | 2.9 | 2.5 | 2.3 | 5.1 | 1.6 |

TABLE 3

|  |  |  | \multicolumn{9}{c}{Examples} |
| --- | --- | --- | --- | --- | --- | --- | --- | --- | --- | --- | --- |
|  |  |  | 15 | 16 | 17 | 18 | 19 | 20 | 21 | 22 | 23 |
| Liquid-retaining layer (%) | Transparent fiber | Tencel bright | 50 | 50 | 50 | 30 | 70 | 60 | 50 | 100 | — |
|  |  | Rayon bright | 50 | — | — | — | — | — | — | — | — |
|  |  | Polyester bright | — | — | 50 | 50 | — | — | 30 | — | — |
|  |  | T-shaped polyester bright | — | — | — | — | — | — | 20 | — | — |
|  |  | Sophista bright | — | 50 | — | — | — | — | — | — | 100 |

TABLE 3-continued

| | | | Examples | | | | | | | | |
|---|---|---|---|---|---|---|---|---|---|---|---|
| | | | 15 | 16 | 17 | 18 | 19 | 20 | 21 | 22 | 23 |
| Opaque fiber | | Tencel dull | — | — | — | — | 30 | 40 | — | — | — |
| | | Rayon dull | — | — | — | — | — | — | — | — | — |
| | | Polyester semi dull | — | — | — | 20 | — | — | — | — | — |
| | | Sophista semi dull | — | — | — | — | — | — | — | — | — |
| | | Large-fineness rayon dull | — | — | — | — | — | — | — | — | — |
| | | Basis weight (g/m²) | 31 | 50 | 70 | 52 | 50 | 50 | 71 | 70 | 70 |
| Adhesion layer | | PP-MB (g/m²) | — | — | — | — | — | — | — | — | 5 |
| | | Ny-MB (g/m²) | — | — | — | — | — | — | 10 | — | — |
| Transparent layer | | PE lami (g/m²) | — | — | — | — | — | — | — | 14 | — |
| | | PET film (g/m²) | — | — | — | — | — | — | — | — | — |
| Basis weight (g/m²) | | | 31 | 90 | 70 | 52 | 50 | 50 | 81 | 84 | 75 |
| Thickness (μm/sheet) | | | 350 | 680 | 710 | 600 | 610 | 600 | 920 | 830 | 980 |
| Density (g/cm³) | | | 0.09 | 0.09 | 0.10 | 0.09 | 0.08 | 0.08 | — | — | — |
| Void ratio (%) | | | 94 | 95 | 93 | 94 | 95 | 94 | — | — | — |
| $W_1$ (%) | | | 9.2 | 10.6 | 22.5 | 20.4 | 15.2 | 17.9 | 24.0 | 14.9 | 12.6 |
| $W_1 - W_0$ (%) | | | 2.5 | 3.9 | 15.8 | 13.7 | 8.5 | 11.2 | 17.3 | 8.2 | 5.9 |
| Transparency | | | 0.080 | 0.078 | 0.225 | 0.265 | 0.170 | 0.224 | 0.214 | 0.098 | 0.079 |
| Stress at 30% elongation under wetting (CD) (N/5 cm) | | | 5.8 | 3.0 | 3.5 | 2.1 | 4.3 | 4.2 | 3.7 | 4.6 | 2.5 |

TABLE 4

| | | | Comparative Examples | | | | | | | | |
|---|---|---|---|---|---|---|---|---|---|---|---|
| | | | 1 | 2 | 3 | 4 | 5 | 6 | 7 | 8 | 9 |
| Liquid-retaining layer (%) | Transparent fiber | Tencel bright | — | — | — | — | — | — | — | — | — |
| | | Rayon bright | — | — | 50 | — | — | — | — | — | — |
| | | Polyester bright | — | — | — | — | — | — | — | — | — |
| | | T-shaped polyester bright | — | — | — | — | — | — | — | — | — |
| | | Sophista bright | — | — | — | — | — | — | — | — | — |
| | Opaque fiber | Tencel dull | 100 | — | — | — | 30 | — | — | 100 | — |
| | | Rayon dull | — | 100 | 50 | — | 50 | — | — | — | — |
| | | Polyester semi dull | — | — | — | 100 | 20 | — | — | — | 100 |
| | | Sophista semi dull | — | — | — | — | — | — | 100 | — | — |
| | | Large-fineness rayon dull | — | — | — | — | — | 100 | — | — | — |
| | | Basis weight (g/m²) | 91 | 70 | 90 | 90 | 70 | 50 | 70 | 30 | 30 |
| Adhesion layer | | PP-MB (g/m²) | — | — | — | — | — | — | — | — | — |
| | | Ny-MB (g/m²) | — | — | — | — | — | — | — | — | — |
| Transparent layer | | PE lami (g/m²) | — | — | — | — | — | — | — | — | — |
| | | PET film (g/m²) | — | — | — | — | — | — | — | — | — |
| Basis weight (g/m²) | | | 91 | 70 | 90 | 90 | 70 | 50 | 70 | 30 | 30 |
| Thickness (μm/sheet) | | | 880 | 770 | 720 | 980 | 680 | 450 | 720 | 320 | 350 |
| Density (g/cm³) | | | 0.10 | 0.21 | 0.13 | 0.09 | 0.10 | 0.11 | 0.10 | 0.09 | 0.09 |
| Void ratio (%) | | | 93 | 94 | 92 | 93 | 93 | 93 | 93 | 94 | 94 |
| $W_1$ (%) | | | 41.8 | 35.3 | 32.2 | 41.7 | 38.9 | 30.8 | 37.3 | 18.2 | 18.0 |
| $W_1 - W_0$ (%) | | | 35.1 | 28.6 | 25.5 | 35.0 | 32.2 | 24.1 | 30.6 | 11.5 | 11.3 |
| Transparency | | | 0.386 | 0.409 | 0.284 | 0.389 | 0.460 | 0.482 | 0.438 | 0.385 | 0.379 |
| Stress at 30% elongation under wetting (CD) (N/5 cm) | | | 6.1 | 4.8 | 6.2 | 3.3 | 5.0 | 3.6 | 2.5 | 1.8 | 1.5 |

TABLE 5

| | | | Comparative Examples | | Reference Example |
|---|---|---|---|---|---|
| | | | 10 | 11 | 1 |
| Liquid-retaining layer (%) | Transparent fiber | Tencel bright | — | — | 100 |
| | | Rayon bright | — | — | — |
| | | Polyester bright | — | — | — |
| | | T-shaped polyester bright | — | — | — |
| | | Sophista bright | — | — | — |

TABLE 5-continued

|  |  | Comparative Examples | | Reference Example |
|---|---|---|---|---|
|  |  | 10 | 11 | 1 |
| Opaque fiber | Tencel dull | — | — | — |
|  | Rayon dull | — | — | — |
|  | Polyester semi dull | — | — | — |
|  | Sophista semi dull | — | — | — |
|  | Large-fineness rayon dull | — | — | — |
|  | Basis weight (g/m²) | 31.3 | 47.8 | 202 |
| Adhesion layer | PP-MB (g/m²) | — | — | — |
|  | Ny-MB (g/m²) | — | — | — |
| Transparent layer | PE lami (g/m²) | — | — | — |
|  | PET film (g/m²) | — | — | — |
| Basis weight (g/m²) | | 31.3 | 47.8 | 202 |
| Thickness (μm/sheet) | | 450 | 530 | 1780 |
| Density (g/cm³) | | 0.07 | 0.09 | 0.11 |
| Void ratio (%) | | 95 | 94 | 92 |
| $W_1$ (%) | | 9.2 | 10.3 | 33.4 |
| $W_1$-$W_0$ (%) | | 2.5 | 3.6 | 26.7 |
| Transparency | | 0.081 | 0.076 | 0.132 |
| Stress at 30% elongation under wetting (CD) (N/5 cm) | | 0.1 | 1.4 | 12.3 |

As apparent from the results shown in Tables 1 to 5, the liquid-retaining sheets of Examples had an excellent transparency in a wet state. In contrast, the liquid-retaining sheets of Comparative Examples 1 to 9 had a low transparency. Moreover, the liquid-retaining sheets of Comparative Examples 10 and 11 had an excellent transparency, while the sheets had a small initial tensile strength under wetting due to gelation. Thus these sheets were not suitable for a facial mask.

FIG. 1 shows a photographic comparison of wet states of the liquid-retaining sheets obtained in Example 2 and Comparative Example 1. In FIG. 1, the left sheet is the sheet of Comparative Example 1, the right sheet is the sheet of Example 2, and the right side of each sheet is in a wet state (water content: 700%). As apparent from FIG. 1, the transparency of the liquid-retaining sheet of Example 1 in a wet state is higher than that of the liquid-retaining sheet of Comparative Example 1.

INDUSTRIAL APPLICABILITY

The liquid-retaining sheet of the present invention absorbs a liquid component and is available for an application for contacting with the skin, for example, a sheet for absorbing a body fluid (e.g., a surface material for a sanitary napkin or a diaper, a diaper liner, and a wet wipe), a skin care sheet (e.g., a facial mask, a makeup-removing sheet), and a cleansing sheet or a body-washing sheet (e.g., a sweat-wiping sheet, and an oil-blocking sheet), a cooling sheet, and a medicated sheet (e.g., an itching-controlling sheet and a wet compress). In particular, the liquid-retaining sheet of the present invention is highly transparent in a wet state and can easily show the adhesion state of the sheet with the skin. Thus, the sheet is particularly useful for a mask impregnated with an effective ingredient (such as a moisturizing or skin-whitening component for the entire face, nose, eyes, lip, neck, and others), a cleansing sheet for removing and wiping a makeup, a medicated or therapeutic sheet impregnated with a blood-circulation-promoting component or an itching-controlling component for skin, a cooling sheet impregnated with a volatile liquid, which uses the evaporation heat of the liquid for cooling, and others.

Further, the liquid-retaining sheet of the present invention is not particularly limited to an application to the human body, in which the sheet is allowed to contact with skin. The liquid-retaining sheet does not drip a liquid even under impregnation with the liquid and can be attached for a long period of time, and thus the liquid-retaining sheet is also available for other applications that make use of such advantages. Specifically, the liquid-retaining sheet is usable for grease-cutting at or around a cooking range, easy softening and removing of bird's droppings attached to a window (windowpane) of an automobile, or removing of mildew stains from tiles and grout (bleaching). In a case where the liquid-retaining sheet of the present invention is used for these applications, a target to be removed shows through the liquid-retaining sheet due to the transparency of the liquid-retaining sheet, and thus the liquid-retaining sheet allows the target to be retained efficiently in a highly wet state without missing the target.

The invention claimed is:

1. A liquid-retaining sheet comprising a liquid-retaining layer that is able to absorb a liquid component and an adhesion layer over a side of the liquid-retaining layer,
   wherein the liquid-retaining layer comprises a nonwoven structural member comprising a transparent fiber that comprises a solvent-spinning cellulose fiber and has a coloring agent content of not more than 0.1% by mass, wherein the proportion of the solvent-spinning cellulose fiber is not less than 50% by mass in the liquid-retaining layer,
   the adhesion layer comprises a meltblown nonwoven fabric that comprises a transparent fiber having a coloring agent content of not more than 0.1% by mass, and the liquid-retaining sheet has a transparency of not more than 0.27,
   wherein transparency=whiteness (%) of a sheet impregnated with 700% by mass of water relative to the sheet mass/basis weight (g/rm²), and the whiteness of the sheet is 1 to 35%.

2. The liquid-retaining sheet according to claim 1, wherein the solvent-spinning cellulose fiber is substantially free from a carboxyl group.

3. The liquid-retaining sheet according to claim 1, wherein the transparent fiber that comprises a solvent-spinning cellulose fiber further comprises a rayon fiber.

4. The liquid-retaining sheet according to claim 1, wherein the proportion of the solvent-spinning cellulose fiber is not less than 90% by mass in the liquid-retaining layer.

5. The liquid-retaining sheet according claim 1, wherein the transparent fiber that comprises a solvent-spinning cellulose fiber is free of coloring agent.

6. The liquid-retaining sheet according to claim 1, wherein said transparent fiber that comprises a solvent-spinning cellulose fiber comprises a positive amount of said coloring agent, and wherein the coloring agent comprises titanium oxide.

7. The liquid-retaining sheet according to claim 1, wherein the nonwoven structural member comprises a staple fiber with an average fiber diameter of 1 to 15 μm.

8. The liquid-retaining sheet according to claim 7, wherein the staple fiber has an average fiber length of 20 to 70 mm, and the nonwoven structural member has an apparent density of 0.08 to 0.15 g/cm$^3$ and a void ratio of 90 to 95%.

9. The liquid-retaining sheet according to claim 1, wherein the nonwoven structural member comprises a spunlace nonwoven fabric obtained by hydroentangling a semi-random web, a parallel web, or a cross web.

10. The liquid-retaining sheet according claim 1, wherein the nonwoven structural member has a basis weight of 30 to 100 g/m$^2$.

11. The liquid-retaining sheet according to claim 1, which further comprises a nonporous transparent layer over a first side of the liquid-retaining layer, wherein the nonporous transparent layer comprises a transparent resin.

12. The liquid-retaining sheet according claim 1, which has a stress at 30% elongation of not less than 1.5 N/5 cm in a direction under wetting in accordance with JIS L 1913.

13. The liquid-retaining sheet according claim 1, wherein the whiteness (%) of the sheet impregnated with 700% by mass of water relative to the sheet mass is 1 to 10%.

14. The liquid-retaining sheet according to claim 1, wherein the liquid-retaining layer is impregnated with a liquid component.

15. The liquid-retaining sheet according to claim 14, which is a skin care sheet that comprises the liquid-retaining layer impregnated with the liquid component, wherein the liquid component comprises a cosmetic preparation.

16. The liquid-retaining sheet according to claim 15, which is a facial mask.

17. The liquid-retaining sheet according to claim 1, wherein the solvent-spinning cellulose fiber has a carboxyl group average substitution degree of not more than 0.03.

18. The liquid-retaining sheet according to claim 1, wherein the transparent fiber that comprises a solvent-spinning cellulose fiber and the transparent fiber of the meltblown nonwoven fabric have the same coloring agent content.

19. The liquid-retaining sheet according to claim 5, wherein the transparent fiber that comprises a solvent-spinning cellulose fiber and the transparent fiber of the meltblown nonwoven fabric have the same coloring agent content.

20. The liquid-retaining sheet according to claim 1, wherein the whiteness of the sheet is 8 to 20%.

* * * * *